United States Patent [19]
Burk et al.

[11] Patent Number: 4,710,483
[45] Date of Patent: Dec. 1, 1987

[54] NOVEL CARBONACEOUS MATERIAL AND PROCESS FOR PRODUCING A HIGH BTU GAS FROM THIS MATERIAL

[75] Inventors: Maksymilian Burk; Jack L. Blumenthal, both of Los Angeles, Calif.

[73] Assignee: TRW Inc., Redondo Beach, Calif.

[21] Appl. No.: 682,459

[22] Filed: Dec. 17, 1984

Related U.S. Application Data

[60] Division of Ser. No. 99,789, Dec. 3, 1979, abandoned, which is a continuation-in-part of Ser. No. 917,240, Jun. 20, 1978, abandoned, which is a continuation-in-part of Ser. No. 817,647, Jul. 21, 1977, abandoned.

[51] Int. Cl.⁴ .................. B01J 23/74; B01J 27/22; C10J 3/00; C10K 3/04
[52] U.S. Cl. .................. 502/185; 48/197 R; 48/203; 60/39.02; 502/177; 502/438; 518/719; 518/720; 518/721
[58] Field of Search .................. 502/177, 185, 438; 585/733; 518/220, 221; 423/447.5, 459

[56] References Cited

U.S. PATENT DOCUMENTS

| | | | |
|---|---|---|---|
| 1,964,744 | 7/1934 | Odell .................. | 154/60 |
| 2,008,270 | 7/1935 | Willekens .................. | 423/459 |
| 2,409,235 | 10/1946 | Alwell . | |
| 2,537,496 | 1/1951 | Watson .................. | 260/676 |
| 2,544,574 | 3/1951 | Walker et al. . | |
| 2,686,819 | 8/1954 | Johnson .................. | 423/439 |
| 2,691,573 | 10/1954 | Mayland .................. | 48/210 |
| 2,694,623 | 11/1954 | Welty, Jr. et al. .................. | 48/197 |
| 3,031,287 | 4/1962 | Benson et al. .................. | 48/197 |
| 3,446,865 | 5/1969 | Roth et al. .................. | 252/447 |
| 3,816,609 | 6/1974 | Itamner .................. | 423/655 |
| 3,847,963 | 11/1974 | Lalancette .................. | 252/447 |
| 3,861,885 | 1/1975 | Schora .................. | 44/1 R |
| 4,134,907 | 1/1979 | Stephens, Jr. .................. | 48/197 R |
| 4,137,373 | 1/1979 | Julan et al. .................. | 252/447 |
| 4,242,103 | 12/1980 | Rabo et al. .................. | 48/197 R |
| 4,242,104 | 12/1980 | Frost et al. .................. | 502/438 |
| 4,583,299 | 4/1986 | Brooks .................. | 502/182 |
| 4,591,334 | 5/1986 | Brooks .................. | 502/182 |
| 4,642,125 | 2/1987 | Bork et al. .................. | 48/197 R |
| 4,650,657 | 3/1987 | Brooks .................. | 423/461 |

FOREIGN PATENT DOCUMENTS

| | | | |
|---|---|---|---|
| 19549 | of 1929 | Australia .................. | 252/445 |
| 154057 | 11/1953 | Australia . | |
| 167059 | 2/1956 | Australia . | |
| 503604 | 11/1934 | Canada . | |
| 101466 | of 1965 | Canada . | |

(List continued on next page.)

OTHER PUBLICATIONS

Renshaw et al., Disproportionation of CO Over Cobalt and Nickel Single Crystams, J. Catalysis, 1971, pp. 394–400.

Coen, F., Literature Survey of C Deposition from CO, 12/61, Dragon Project Report.

Walker et al, Carbon Formation for Carbon Monoxide-Hydrogen Mixtures, J. Phys. Chem. 3, Jan.-Jun. 1959, 133–149.

Donald H. Tach, Annotated Bibliography of the Literature and Patents Relating to the Production of Carbon by the Decomposition of Carbon Monoxide, Mellon Institute, Pittsburgh, Pa. (1956).

*Primary Examiner*—Paul E. Konopka
*Attorney, Agent, or Firm*—Jeffery G. Sheldon; Shlomo R. Friedman; Benjamin DeWitt

[57] ABSTRACT

Disclosed is a carbonaceous material which reacts rapidly with hydrogen to produce a methane-rich gas containing at least 20% by volume methane. The carbonaceous material is formed by contacting a carbon monoxide containing gas with an initiator including a ferrous group metal such as iron, cobalt, or nickel. The carbonaceous material grows from the surface of the initiator as fibers which include a ferrous metal component derived from the initiator. This ferrous metal component, which may be a metal, an alloy, a carbide, or other metallic substance, is dispersed throughout the carbon network as small nodules which are at least partially bonded to the carbon.

24 Claims, 19 Drawing Figures

FOREIGN PATENT DOCUMENTS

| | | |
|---|---|---|
| 0004456 | 7/1982 | European Pat. Off. . |
| 2014695 | 10/1971 | Fed. Rep. of Germany . |
| 729461 | 4/1932 | France . |
| 758824 | 11/1933 | France . |
| 978243 | 11/1952 | France . |
| 1437061 | 5/1965 | France . |
| 2048971 | 3/1971 | France . |
| 2398108 | 2/1979 | France . |
| 79983 | 12/1978 | Luxembourg . |
| 6506948 | 12/1965 | Netherlands . |
| 160561 | 5/1921 | United Kingdom . |
| 252152 | 5/1926 | United Kingdom . |
| 268853 | 4/1927 | United Kingdom . |
| 294759 | 8/1928 | United Kingdom ................ 423/459 |
| 308351 | 4/1930 | United Kingdom . |
| 359175 | 10/1931 | United Kingdom ................ 423/459 |
| 581569 | 10/1946 | United Kingdom . |
| 791602 | 3/1958 | United Kingdom . |
| 1028965 | 5/1966 | United Kingdom . |
| 1119640 | 7/1968 | United Kingdom . |
| 1269743 | 4/1972 | United Kingdom . |
| 1278119 | 6/1972 | United Kingdom . |
| 1327783 | 8/1973 | United Kingdom . |
| 1403992 | 8/1975 | United Kingdom . |
| 1479521 | 7/1977 | United Kingdom . |

OTHER PUBLICATIONS

Gillrand, E. R. et al, Reactivity of Deposited Carbon, Ind. & Engr. Chem., Oct. 1957, pp. 2195–2262.

Ruston, W. R. et al, The Solid Reaction Products of the Catalytic Decomposition of Carbon Monoxide on Iron at 550° C., *Carbon,* 1969, 7:47–57, Organic Chemistry, p. 66.

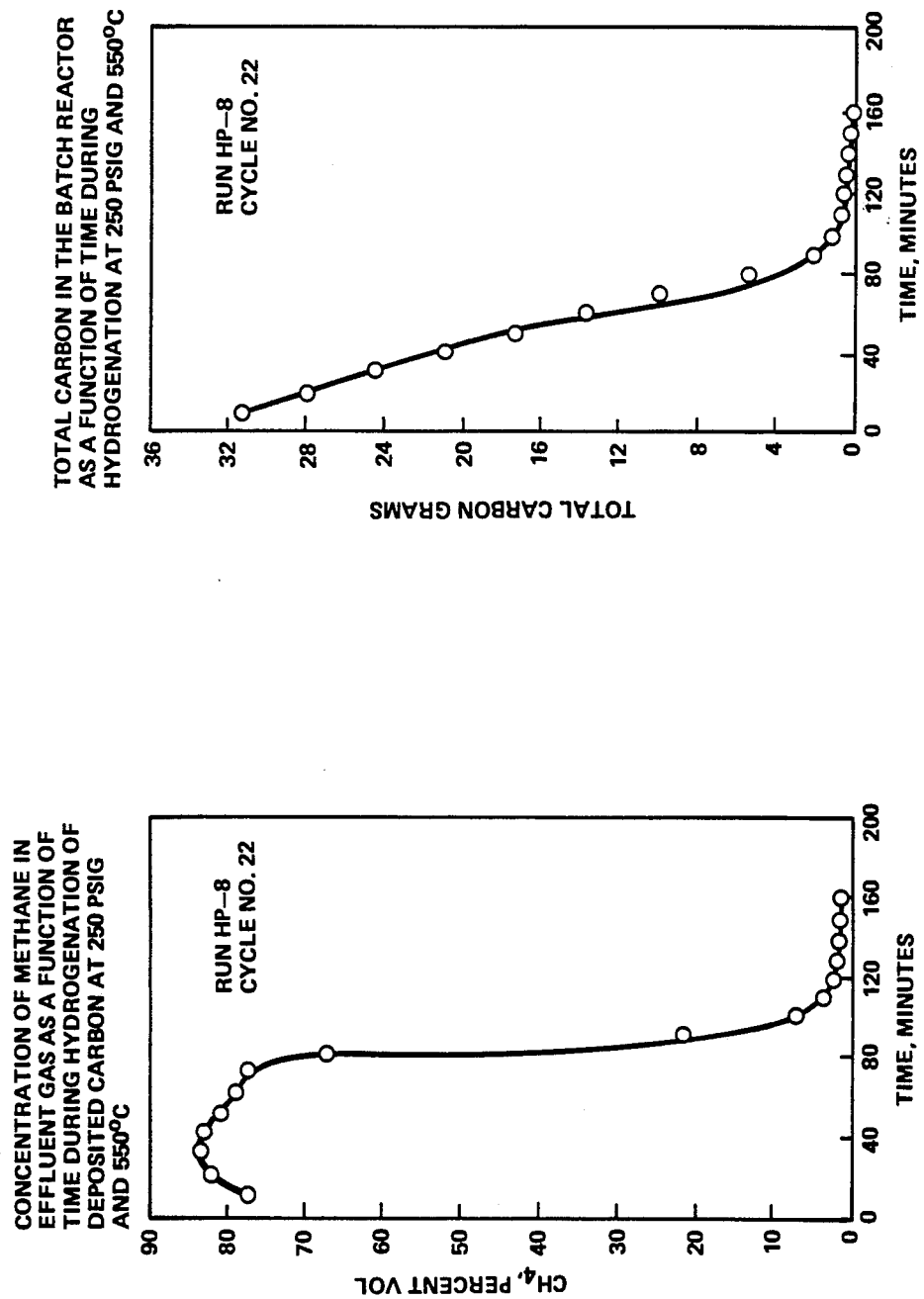

NOVEL CARBONACEOUS MATERIAL AND PROCESS FOR PRODUCING A HIGH BTU GAS FROM THIS MATERIAL

RELATED PATENT APPLICATIONS

This application is a division of application Ser. No. 099,789 filed Dec. 3, 1979, now abandoned. Application Ser. No. 099,789 is a continuation-in-part of U.S. patent application, Ser. No. 917,240, filed June 20, 1978, and entitled "Novel Carbonaceous Material and Process for Producing a High Btu Gas from this Material," which is a continuation-in-part of U.S. patent application, Ser. No. 817,647, filed July 21, 1977, and entitled "Novel Carbonaceous Material and Process for Producing a High Btu Gas from this Material," both of which are incorporated herein by reference and both of which are now abandoned.

BACKGROUND OF THE INVENTION

Various forms of carbons are well-known and have been used as pigments, sources of coke, chemical absorbers, etc. One type of carbon forms through the disproportionation of carbon monoxide in the presence of a ferrous group metal. As used herein, "disproportionation" means any of the reactions which occur in the presence of a ferrous group metal to produce carbon from a carbon monoxide containing gas, which may also contain hydrogen and other substances. The following are typical reactions:

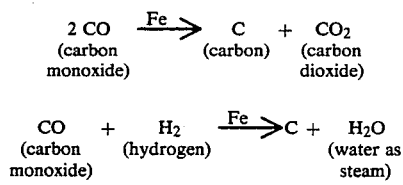

In the past, the carbon formed by disproportionation has had little commercial value. In many chemical processes, such as processes involving the Fischer-Tropsch synthesis, the formation of such carbon through disproportionation is an undesirable side reaction and may even deactivate the catalyst used in such processes due to carbon deposition on the catalyst.

It is known that carbon will react with hydrogen to form methane ($CH_4$), the main ingredient of natural gas. But the known carbons have such a slow reaction rate at temperatures where high methane concentrations are thermodynamically allowable that experts consider a commercial process to produce methane based on this reaction as unfeasible. Demand for methane has, however, increased and almost outstripped the supply. Consequently, a process to synthesize methane would be of great benefit to the economy.

It has been proposed that methane may be produced from coal, and, consequently, extensive research is being conducted to find economical ways to convert coal into methane. For example, methane has been made from a synthesis gas of carbon monoxide and hydrogen produced by burning coal in a mixture of oxygen and steam. Oxygen is used rather than air so that the synthesis gas will not contain substantial amounts of nitrogen, a major ingredient of air, because nitrogen cannot be readily separated from the synthesis gas or the methane product. One disadvantage of this process is that costly oxygen plants are required. Moreover, the carbon dioxide produced in the premethanation steps of the process is removed from the carbon monoxide-hydrogen feed stream. This involves a relatively expensive gas separation step.

THE INVENTION

We have discovered novel types of carbon, referred to herein as carbonaceous material, which, according to our process, react rapidly with hydrogen to form methane. In our process we are able to produce methane-rich gas streams containing at least 20% by volume methane and can easily produce methane-rich gas streams containing 75% or more by volume methane. We can achieve this because the carbonaceous material has the ability to cycle between carbon-rich and carbon-lean states. This is essential to the commercial success of our process. The reaction of the carbonaceous material with hydrogen depletes the material of carbon, which is replenished by disproportionation of carbon monoxide. The carbonaceous material exhibits the unexpected ability to be cycled between a carbon-rich state and a carbon-lean state while at the same time experiencing a significant increase in reactivity with hydrogen. This increase in reactivity continues through several cycles and then stabilizes. Furthermore, essentially all of the material is reactive with hydrogen at elevated temperatures. Thus, an accumulation of dead or unreacted material, leading to the shutdown of our process, is avoided. Our process can be carried out in reasonably sized reactors at reasonable throughput to provide a product gas stream with a heating value of 500 or more British thermal units (Btu's) of heat per standard cubic foot of product gas.

BRIEF DESCRIPTION OF THE DRAWINGS

FIG. 13 shows the concentration of methane in effluent gas as a function of time during hydrogenation of deposited carbon at 250 p.s.i.g. and 550° C.

FIG. 14 shows the total carbon in the batch reactor as a function of time during hydrogenation at 250 p.s.i.g. and 550° C.

CARBONACEOUS MATERIAL

General

Figure 1:
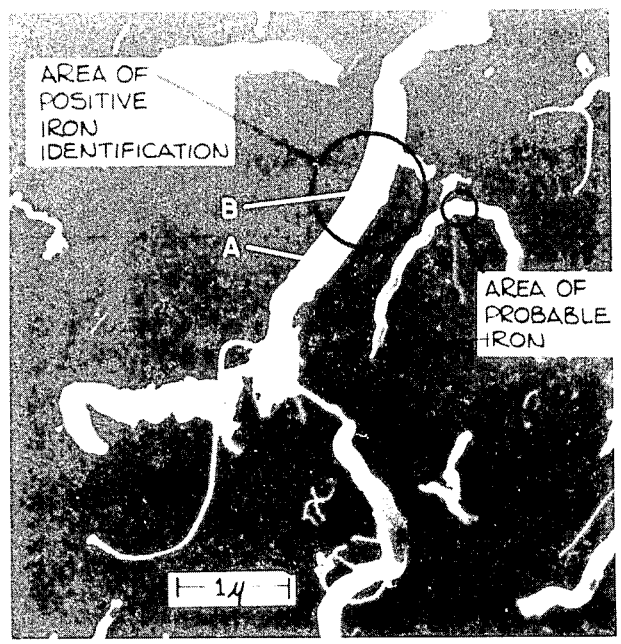
FIG. 1 is a micrograph showing some of the fibers of carbonaceous material under relatively high magnification using a scanning electron microscope.

The carbonaceous material is fibrous, with many of the fibers having two phases. One phase, usually the major phase, is rich in carbon which, as discussed later, is partially graphitized. The other phase, usually the minor phase, is rich in a ferrous group metal component. The carbon-rich phase provides a partly crystallized network, and the ferrous group metal component is dispersed randomly throughout the carbon network as nodules. At least some of the dispersed ferrous group metal component is bonded to the carbon. Some of this component may occupy spaces in the network between the planes of the graphitized carbon.

The nodules of the ferrous group metal component are in the form of ferrous metals, or alloys including a ferrous metal, and these ferrous metals or alloys are in the metallic or carbidic state. The nodules are dispersed in, and at least partially bonded to, the carbon, and we believe they perform a dual catalytic function, the first to catalyze the formation of the carbonaceous material by disproportionation of carbon monoxide and the second to catalyze the reaction of hydrogen and the carbonaceous material to form methane. To attain both types of catalytic activity, it appears that the ferrous group metal component should be present in an amount of at least 0.5 weight percent based on the total weight of the material. Preferably, the ferrous group metal component should comprise at least 2.0 weight percent of the total weight of the material. When the ferrous group metal is present in this amount, the carbon in the material reacts with hydrogen to form methane at a methanation rate of at least 0.1 mole of methane formed per hour per mole of carbon present when the carbon is contacted with hydrogen at a temperature of 550° C., one atmosphere pressure, and a minimum hydrogen feed rate of 2 moles of hydrogen per hour per mole of carbon present.

As will be discussed later in detail, the reactivity of the carbonaceous material may be enhanced by 3 to 20 or more times over carbonaceous material which has not been cycled between carbon-rich and carbon-lean states. This enhanced reactivity with hydrogen is a distinguishing characteristic of our materials, and is substantially higher than that of other forms of carbon. Moreover, our materials maintain their high rate of reactivity even after being substantially depleted of, or enriched in, carbon. Water vapor has an effect on the reactivity of our material, and under some conditions may impede the rate at which methane is formed. Consequently, at atmospheric pressure, the hydrogen should contain less than about 1% water vapor by volume. Ingredients in the hydrogen which, in the presence of the carbonaceous material react to form water, should also be avoided. For example, carbon monoxide in the presence of the carbonaceous material reacts with hydrogen to form methane and water.

Carbonaceous material of our invention may be initially formed by passing carbon monoxide over a bulk metal initiator selected from the group consisting of (a) iron (Fe), cobalt (Co), and nickel (Ni) and mixtures thereof, (b) oxides of iron, cobalt, and nickel, such as cobalt oxide, nickel oxide, ferrous oxide, ferric oxide, and mixtures thereof, (c) alloys including iron, cobalt or nickel, or alloys of any two or all of these metals, and mixtures of such alloys, (d) ores of iron, cobalt, and nickel, and mixtures of such ores, and (e) mixtures of any two or more of the foregoing. The bulk metal initiator is the source of, and should be distinguished from, the ferrous group metal component in the carbonaceous material formed.

Examples of the bulk metal initiators, and the forms those initiators take, are: ferroso-ferric oxide ($Fe_3O_4$) powder, hematite type iron ore composed mostly of $Fe_2O_3$, electrolytic iron chips, carbon steel spheres, steel wool, nickel oxide, cobalt oxide, high purity nickel chips, high purity cobalt chips, iron-nickel alloy buttons, iron-cobalt alloy buttons, and stainless steel. We have used Mesabi Range iron ore with good results. The use of such ore and the like is desirable because it is readily available and inexpensive. Alternatively, the bulk metal initiator may be supported on a high surface area (for example, in excess of 50 square meters per gram) substrate without adversely affecting the formation of the carbonaceous material. Silica and alumina are typical substrates. Indeed, when the bulk metal initiator is highly dispersed, for example being supported on a high surface area alumina, the resulting carbonaceous material is even more reactive with hydrogen than the carbonaceous material initially formed on lower surface area bulk metal initiators.

For the carbonaceous material to have the desired reactivity, it appears that it should be formed in-situ. That is, simply mixing the bulk metal initiator with carbon does not result in our carbonaceous material. Exposure of the bulk metal initiator to a carbon monoxide-containing gas at a temperature of between about 300° C. and about 700° C., preferably 400° C. to 600° C., produces the carbonaceous material. The pressure may vary between about 1 and about 100 atmospheres, but the preferred range is from 1 to 25 atmospheres. Preferably, the carbon monoxide-containing gas includes some hydrogen. Carbon monoxide is maintained in contact with the bulk metal initiator until substantial amounts of carbonaceous material deposit on the initiator. If a pure metal or metal alloy is used as the initiator rather than a metal oxide, carbon deposition initially proceeds very slowly. Pre-oxidation of the metal or metal alloy at 900° C. in air for two minutes increases significantly the rate at which carbon deposition proceeds.

When iron oxides are used as the bulk metal initiator, they are first reduced by the carbon monoxide-hydrogen feed gas and then the carbonaceous material begins to collect on the initiator. Consequently, the length of time the carbon monoxide-containing gas contacts the iron oxide is important. If, for example, $Fe_3O_4$ is used and the carbon monoxide containing gas is at 600° C. and one atmosphere, initially the iron oxide is at least partially reduced. This is indicated by a loss of weight of iron oxide due to the loss of oxygen. For example, after the iron oxide was contacted with pure carbon monoxide gas for 15 minutes, the sample had a weight loss of about 22% (oxygen comprising about 27.6% by weight of the iron oxide) and little carbonaceous material was deposited on the bulk metal initiator. The carbon that was deposited was in the form of iron carbide. After 30 minutes of contact, the sample had a 15% weight loss and the carbon deposited on it was in the carbide form, primarily $Fe_3C$. Even after 60 minutes of contacting the iron oxide with carbon monoxide, the sample still showed a weight loss of about 10%, and substantially all of the carbon deposited on the iron oxide was in the carbide form, again primarily as $Fe_3C$. After 4 hours, however, the sample had about a 75% weight gain and the deposited carbonaceous material was a mass of fibers, many of which had a major phase of carbon and a minor phase of the ferrous group metal component.

Typically, the carbonaceous material grows from the surface of the initiator as fibers, possibly hollow fibers. Many of the fibers have a diameter in the range of about 0.02 micron to about 2.0 microns and a length to diameter ratio greater than about 5:1. In analyzing these fibers we found that they frequently contained one or more nodules of alpha-iron, iron carbide, iron/nickel alloy, or iron/cobalt alloy, depending on the initiator used. The ferrous group metal component is transported into the fibers during formation of the carbonaceous material. This transported ferrous group metal component is no longer physically associated with the bulk metal initiator and is apparently an essential part of our highly reactive carbonaceous material and appears to act as a catalyst.

It should be understood that it is difficult to distinguish the active ferrous metal component in the carbonaceous material from the bulk metal initiator when small particles of initiator are used. To assist in understanding what was occurring during formation of the carbonaceous material, we used a metal plate and grew fibers of the material from the surface of the plate. These fibers were then scraped off the surface, permitting us to separate the initiator from the fibers which contained nodules transported from the plate. We conducted a series of tests using plates of iron, nickel, cobalt, an iron-cobalt alloy, and an iron-nickel alloy as the initiator. The carbonaceous material formed as a billowy mound of fibers on the plate, permitting the plate to be simply physically separated from the carbonaceous material. Starting with an iron plate as the initiator, the carbonaceous material scrapped from the plate contained from about 1.0 to about 3.5 percent by weight of dispersed iron component as determined by both spectroscopic analysis and ashing techniques. The balance of the material was principally carbon with small amounts of hydrogen. The carbon was partially graphitized. Partially graphitized carbon has been discussed in detail by R. E. Franklin in his paper published in Acta Cryst, vol. 4, pp 253, (1951).

Figure 2:
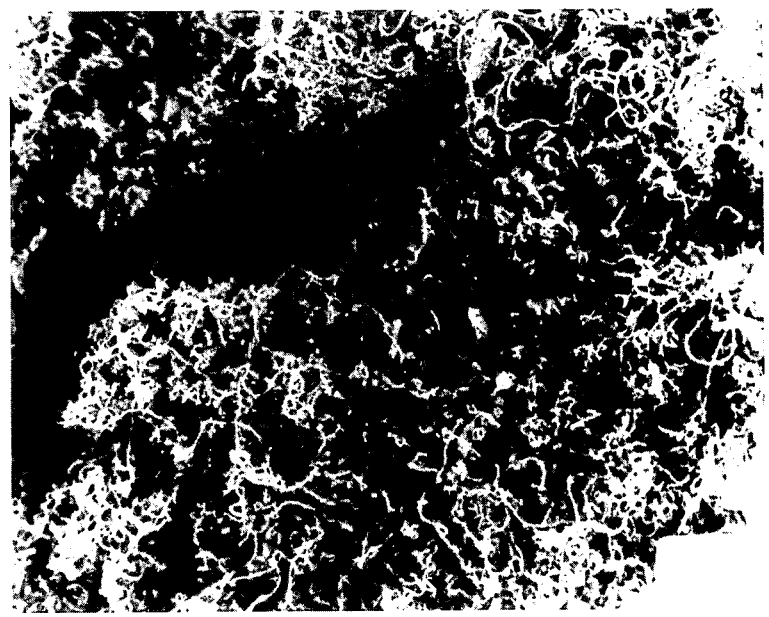
FIG. 2 is a micrograph showing the fibers under relatively low magnification using a scanning electron microscope.

We have examined carbonaceous fibers formed on an iron plate using a scanning electron microscope. FIG. 2 is a micrograph showing fibers of the carbonaceous material as seen through a scanning electron microscope under relatively low magnification. FIG. 1 is a micrograph showing, in greater detail, some of the fibers under relatively high magnification using the scanning electron microscope. In one representative sample fiber, identified as A, an area of high iron concentration was positively identified. Fiber A was scanned in several areas with an electron microprobe analyzer, and the nodule B was positively identified as containing iron. This nodule was about 3000 Å long and about 1000 Å wide. This analysis was made according to the analytical procedures described by J. R. Ogren in "Electron Microprobe," Chapter 6, in *Systematic Materials Analysis,* vol. 1, Academic Press, Inc., New York 1975. Assuming the fiber is solid and it exhibits a density intermediate between that of amorphous and fully graphitized carbon, the detectability limit of the microprobe analysis is about 1.5% by weight iron.

X-ray analysis of the samples of carbonaceous material deposited on iron plates showed iron to be present as a form of iron carbide and, possibly, as an alpha-iron as well. The Debye-Scherrer method was used to obtain powder diffraction patterns on a General Electric Model XRD-5 X-ray spectrometer. As will be discussed later in greater detail, it is desirable to hydrogenate the carbonaceous material initially formed. Using the same method to analyze this hydrogenated material, it was revealed that the X-ray detectable iron in it was present only as alphairon.

As the micrograph in FIG. 1 shows, the iron component is bonded to the carbon. We have attempted to break this bond and separate the iron component from the carbon by simple physical means such as sifting through sieves and pulling the iron from the carbon with magnets. These methods, however, did not achieve separation. Since the iron component in the carbonaceous material cannot be separated from the carbon by simple physical means, this indicates to us that at least a part of the iron is intimately associated with the carbon and at least part of the iron is bonded to the carbon, possibly at the atomic or molecular levels. Or, perhaps the iron is in solid solution in the carbon. If this is so, the interfaces of the iron-carbon solid solution and crystals of the iron component may be active sites which cause the rapid reaction rate during methanation. Whatever bond is formed between the iron and carbon, we have found that iron by itself, activated charcoal by itself, commercial cementite ($Fe_3C$), and a simple physical mixture of iron and activated charcoal do not have the properties of the carbonaceous material of our invention. None of these compounds or mixtures, when contacted with hydrogen at elevated temperatures, will form methane at rates approaching the rates attained using our carbonaceous materials. This is shown in the following Table I, which summarizes the rates of methanation at 550° C. and one atmosphere pressure of several different carbonaceous materials of our invention and compares the results with several control materials including an activated charcoal, coal char, commercial iron carbide, a mixture of activated charcoal and iron powder, and spectroscopic grade graphite powder. In some of the experiments the deposited carbonaceous material was separated from a geometrically well defined bulk metal initiator such as iron foil or steel spheres. In other experiments the deposited carbonaceous material and initiator were not separated prior to the measurement of the rate of methanation. Several key results are apparent from Table I:

way they are prepared (compare Experiment 1 and Experiment 9).

TABLE I

COMPARISON OF METHANATION RATES OF CARBONACEOUS MATERIALS AND OTHER CARBONS

| STARTING MATERIAL | CARBONACEOUS MATERIAL SEPARATED FROM IRON INITIATOR | C/FE ATOM RATIO | METHANATION RATE (MOLES CH$_4$/HR/ MOLE CARBON) |
|---|---|---|---|
| 1. CARBON DEPOSITED FROM CO/H$_2$ GAS STREAM AT 550° C. AND 1 ATM ONTO HIGH PURITY IRON FOIL. | NO | 27.3* | 0.10 |
| 2. CARBONACEOUS MATERIAL FROM SAMPLE 1 SEPARATED FROM FOIL AND REHYDROGENATED. | YES | 176 | 0.10 |
| 3. CARBONACEOUS MATERIAL DEPOSITED ON ¼ INCH CARBON STEEL SPHERES AT 550° C. FROM CO/H$_2$ GAS STREAM AT 1 ATM PRESSURE. | YES | 220 | 0.28 |
| 4. CARBONACEOUS MATERIAL INITIALLY PREPARED BY SEVERAL CYCLES OF CARBON DEPOSITION AND HYDROGENATION AT 550° C. AND PRESSURE FROM ABOUT 7 TO ABOUT 17 ATM OVER 3/16 INCH CARBON STEEL SPHERES. SAMPLE SEPARATED FROM SPHERES AND CARBON DEPOSITED FROM 1 ATM CO/H$_2$ GAS STREAM. | YES | 12.6 | 0.49 |
| 5. MESABI RANGE IRON ORE PRE-REDUCED IN H$_2$ AND THEN USED TO CATALYZE CARBON DEPOSITION FROM CO/H$_2$ GAS STREAM AT 550° C. AND 1 ATM. | NO | 7* | 0.24 |
| 6. SAME AS SAMPLE 5 EXCEPT EXPOSED TO AMBIENT AIR FOR 96 HOURS AT 250° C. BEFORE HYDROGENATION. | NO | 7* | 0.20 |
| 7. CARBONACEOUS MATERIAL DEPOSITED FROM CO/H$_2$ GAS STREAM ON 40-60 MESH SPONGE IRON - FIRST CYCLE OF CARBON DEPOSITION AND SUBSEQUENT HYDROGENATION. | NO | 1.9 | 0.17 |
| 8. SAMPLE #7 AFTER 39 CYCLES OF CARBON DEPOSITION AND HYDROGENATION. | NO | 0.39 | 1.39 |
| 9. CARBONACEOUS MATERIAL DEPOSITED FROM CO/H$_2$ GAS STREAM ON SUPPORTED IRON CATALYST. STARTING MATERIAL CONSISTS OF 14% IRON ON HIGH SURFACE AREA ALUMINA. | NO | 2.6 | 2.13 |
| 10. COMMERCIAL CEMENTITE Fe$_3$C. | — | 0.33 | 0.05 (No CH$_4$ detected) |
| 11. NORTI-A ACTIVATED CHARCOAL. | — | 1000 | 0.0004 |
| 12. CHAR FROM COAL GASIFICATION. | — | 1000 | 0.0004 |
| 13. NORIT-A CHARCOAL MIXED WITH ELECTROLYTIC IRON POWDER 50:50 WT BASIS. | — | 4.7* | 0.0004 |
| 14. SPECTROSCOPIC GRAPHITE POWDER. | — | 10,000 | $10^{-7}$ |

*Includes bulk iron.

(i) The iron foil serves as the catalyst which initiates the carbon deposition, but does not play a significant role in the subsequent hydrogenation of the carbonaceous material (compare Experiments 1 and 2).

(ii) Material which has been cycled several times between a carbon-rich state and a carbon-lean state by alternate carbon deposition and hydrogenation is more reactive with hydrogen (compare Experiments 7 and 8)

(iii) Exposure of deposited carbonaceous material to ambient temperature air does not appear to degrade its activity for hydrogenation (compare Experiments 5 and 6).

(iv) The carbonaceous material prepared by deposition from carbon monoxide containing gas streams is several orders of magnitude more reactive with hydrogen at 550° C. than activated charcoals, coal chars, or mixtures of iron powder and activated charcoal (compare Experiment 3 with Experiments 10 through 14).

(v) Although all of the materials prepared by the disproportionation reaction are reactive with hydrogen, some materials are as much as 20 times more reactive with hydrogen depending on the way they are prepared (compare Experiment 1 and Experiment 9).

One way of thinking about our material is that the ferrous group metal component is a catalyst that is dispersed throughout a carbon matrix. This ferrous group metal component catalyzes the reaction of the carbon in the matrix with other reactants, such as hydrogen. Carbon is depleted as the reaction proceeds, but the material may be replenished with carbon by exposure to a carbon monoxide-containing gas. When exposed at elevated temperatures to carbon monoxide, the active component catalyzes the disproportionation of carbon monoxide.

Figure 3:
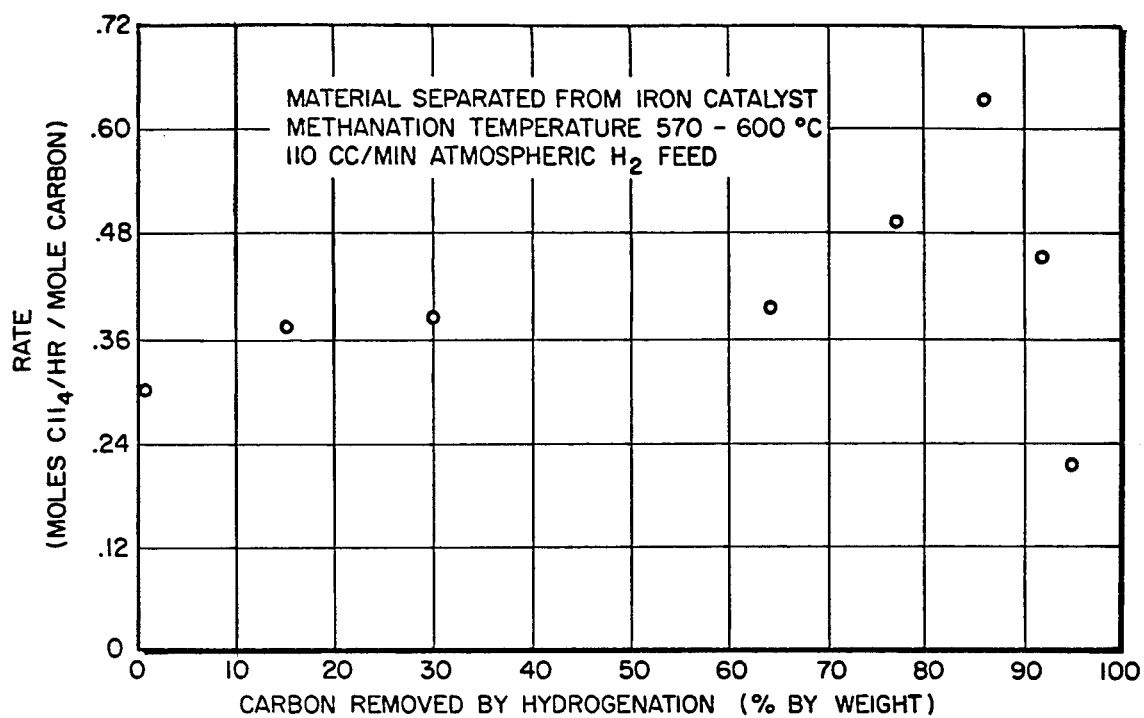
FIG. 3 is a graph depicting the specific methanation rate of the carbonaceous material versus the percent of carbon removed by the hydrogenation of the carbonaceous material.

Even though carbon is depleted from the material by reaction with hydrogen, we have discovered that the material retains its high specific methanation rate. Surprisingly, we have been able to remove almost all the carbon from the carbonaceous material and still maintain a relatively high specific rate of methanation. This property of the material is illustrated by FIG. 3 where the specific methanation rate of the carbonaceous material is plotted against the percent of the carbon removed by hydrogenation of the material. (The rates shown in FIG. 3 were determined at 570°-600° C., and 1 atmosphere pressure.) The carbon-rich material (i.e., the material containing about 96% carbon) had an initial reactivity of about 0.30 moles CH$_4$/hr/mole of carbon. This reactivity gradually increased to about 0.63 moles CH₄/hr/mole of carbon when about 88% of the carbon was removed. When about 90% of the carbon was removed, or when the material contained about 30 weight percent of the iron component, its reactivity decreased rapidly. If the carbon-rich material had contained, initially, 95 weight percent carbon and 5 weight percent iron, the final material, after removal of about 90% carbon, would contain about 35 weight percent of iron. When we methanate our iron-based carbonaceous material to convert over 95% of its carbon to methane, mix the resulting carbon-lean material with particulate carbon (not carbonaceous material obtained from the disproportionation reaction), and then expose this mixture to hydrogen at the pressure and temperature ranges we normally use for methanation, no methane forms.

Based on the above experiments, we have found that the carbonaceous material of our invention may vary in composition approximately as follows:

|  | Operable Range (% by weight) | Preferred Range (% by weight) |
|---|---|---|
| Partially Graphitized Carbon | 30–99.5% | 30–95% |
| Dispersed Ferrous Group Metal Component | 0.5–70% | 5–70% |

Weight percentages were determined after the carbonaceous material was separated from the bulk ferrous group metal.

The carbonaceous materials also retain their properties after extended periods of storage, whether stored in the carbon-enriched or in the carbon-depleted states. However, because exposure of these materials to oxygen may oxidize the ferrous metal group components and thus impair their catalytic activity, we avoid exposing them to air during storage. After we store our iron-based carbonaceous material for 24 hours at room temperature, we observe no deterioration in its rate of methanation.

Figure 9:
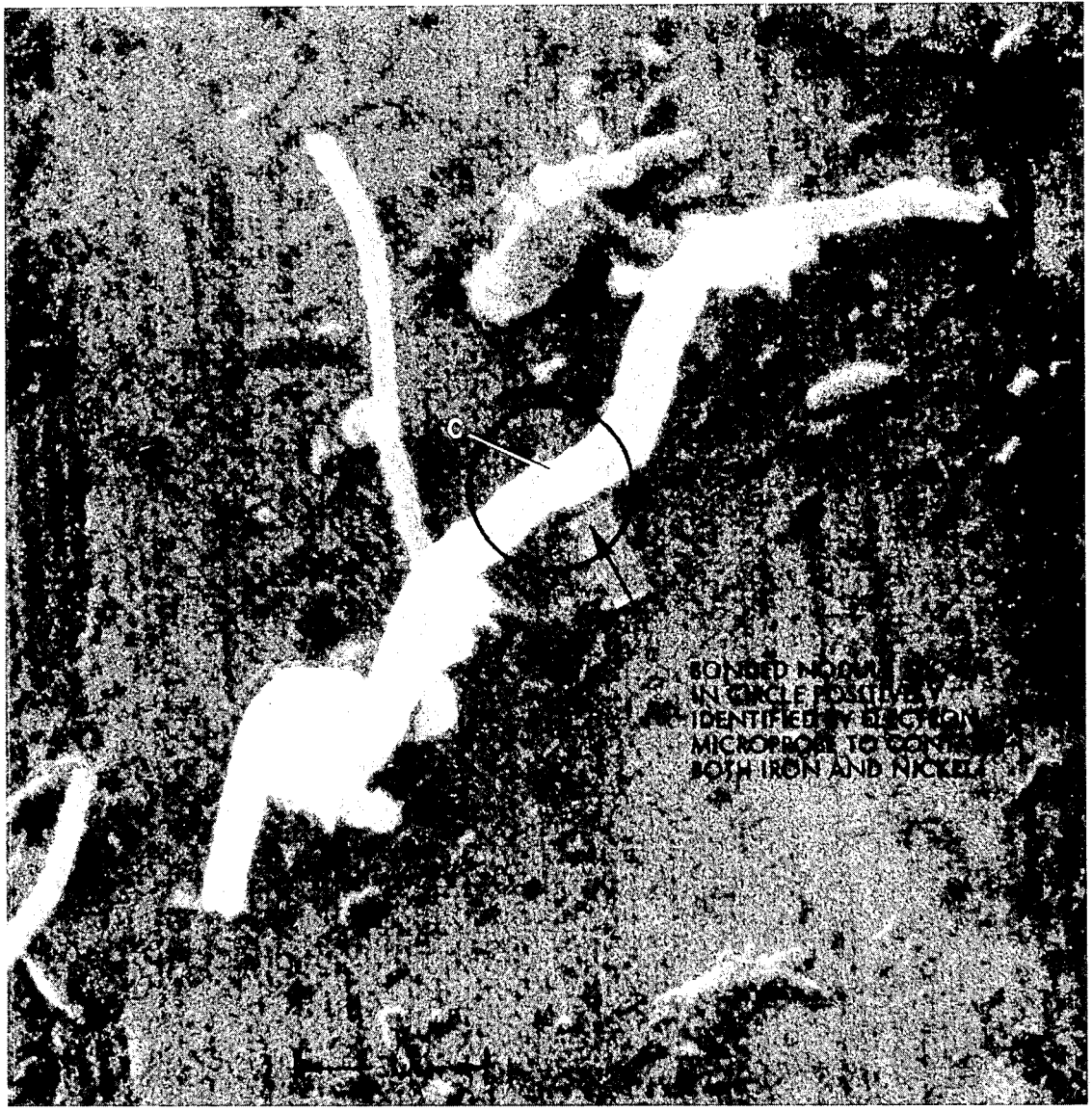
FIG. 9 is a scanning electron micrograph of a carbonaceous material prepared by carbon monoxide disproportionation over an alloy plate consisting of about 50 percent by weight nickel and about 50 percent by weight iron.

Ferrous Metal Alloy Catalysts Supported on High Surface Area Carbonaceous Material FIG. 9 shows a scanning electron micrograph of another of our carbonaceous materials prepared by carbon monoxide disproportionation over an alloy plate consisting essentially of about 50% by weight nickel and about 50% by weight iron. After separating the fibrous carbonaceous material from the alloy plate, the carbonaceous material was found to contain 98.42% by weight C, 0.48% Fe by weight, 0.73% Ni by weight, and 0.94% by weight H (un-normalized data which does not add up exactly to 100%). The area marked by a circle in the micrograph was analyzed with an electron microprobe and was found to contain high concentrations of both iron and nickel in approximately equal amounts. X-ray analysis of a representative sample of the fibers indicated the presence of iron-nickel alloy. It appears likely that the nodule C shown in the circle in FIG. 9 actually consists of an iron-nickel alloy. Whether or not the nodule C shown in FIG. 9 is a true solid solution alloy of iron and nickel, our analysis clearly shows that very small nodules containing both iron and nickel were transported from the alloy plate to the carbon fibers and became intimately associated with and bonded to the fibers.

The material described above is an example of novel carbon supported ferrous metal alloy catalysts which can be prepared through the mechanism of carbon monoxide disproportionation. The bulk metal alloy initiator in the form of plates, balls, and the like would be inactive, or of low activity, as a catalyst. By starting with different bulk metal alloy initiators it is possible to prepare a family of catalysts in which different active ferrous group metal alloy nodules are dispersed or supported on a high surface area fibrous carbonaceous material. For example, the fibrous material shown in FIG. 9 has a surface area of about 200 square meters per gram and contains dispersed, minor phase, iron-nickel alloy nodules bonded to the carbon fibers. These nodules are generally less than 2000 Å on a side. We have obtained similar results starting with iron-cobalt and nickel-cobalt plates of low activity and through carbon monoxide disproportionation obtained carbonaceous materials containing nickel-cobalt and iron-cobalt alloy nodules, active as catalyst, dispersed throughout the carbonaceous fibers. Hence, depending on the choice of bulk metal alloy initiator, it is possible to prepare a wide range of catalytically active, high surface area, ferrous metal alloy nodules supported on and bonded to high surface area fibrous carbonaceous material. We believe these nodules are centers for catalytic activity.

These materials can be enriched in active metal catalyst through the mechanism of hydrogenating away some of the supporting carbon material. For example, it is possible to prepare a catalyst which initially contains 2% iron-nickel alloy nodules and enrich the catalyst to 10% metal content through controlled hydrogenation. In this way, one can obtain active catalytic materials having a controlled metal alloy concentration within the fibrous carbon support. The bulk metal initiator may be separated from the carbonaceous material prior to hydrogenation.

Enhanced Material

It is apparent from Table I that all the carbonaceous materials prepared by the disproportionation reaction are much more reactive with hydrogen at 550° C. to form methane than the other control carbons tested or the physical mixture of carbon with iron. However, even within the group of carbonaceous materials prepared by the disproportionation reaction, the specific rate of methanation of these materials may vary by as much as a factor of 20 or more. At the low end of the rate scale are uncycled carbonaceous materials deposited on bulk metal initiators of relatively low surface area such as plates, spheres, tubes, ores, etc. For our process of producing a high Btu gas, we prefer to use carbonaceous materials having the highest specific methanation rate. We have found at least two ways of obtaining these enhanced materials: They are (1) by starting with a bulk metal initiator which is itself highly dispersed or of high surface area as, for example, an iron supported on high surface area alumina (Experiment 9 of Table I), or (2) by cycling the initially deposited carbonaceous material between carbon-rich states and carbon-lean states by alternately depositing carbonaceous material by disproportionation and removing carbon by hydrogenation (Experiment 8 in Table I).

In the enhanced carbonaceous material the ferrous group metal component is sufficiently dispersed throughout the carbon as nodules which are intimately associated with, and at least partially bonded to, the carbon, so that the material is characterized in that the carbon present in the material will react with hydrogen to form methane at a rate exceeding 0.3 mole of methane formed per hour per mole of carbon present when the carbon is contacted with hydrogen at a temperature of 550° C., one atmosphere pressure, and a minimum hydrogen feed rate of 2 moles of hydrogen per hour per mole of carbon present. We can readily make carbonaceous material which will react with hydrogen to form methane at a rate exceeding 1.0 mole of methane formed per hour per mole of carbon present when the carbon is contacted with hydrogen at a temperature of 550° C., at one atmosphere pressure, and a minimum hydrogen feed rate of 20 moles of hydrogen per mole of carbon present. Another characterizing feature of the material is that during disproportionation it exhibits a carbon deposition rate exceeding 10 grams of carbon per hour per gram of ferrous group metal component present when contacted with a gas consisting essentially of 80% by volume carbon monoxide and 20% by volume hydrogen, at 500° C., one atmosphere pressure, and a minimum feed rate of 10 moles of carbon monoxide per hour per gram of ferrous group metal component present. Under some conditions, we have observed the formation of this material when about 15% by weight of the carbon was removed by hydrogenation of the carbonaceous material initially prepared. This material preferably is again subjected to carbon deposition and a second hydrogenation. Moreover, the hydrogen used normally should contain not more than about 1% water by volume.

In the case of an initially high surface area bulk metal initiator, we believe that more ferrous metal component is transported from the initiator to the carbon fibers per unit weight of fibers. In the case of cycling already prepared carbonaceous material between carbon-lean and carbon-rich states, it is postulated that the average size of the active nodule within the fibers decreases with cycling, thus resulting in more active nodules of greater surface area and hence more activity per unit weight of ferrous group metal component.

Figure 10A:
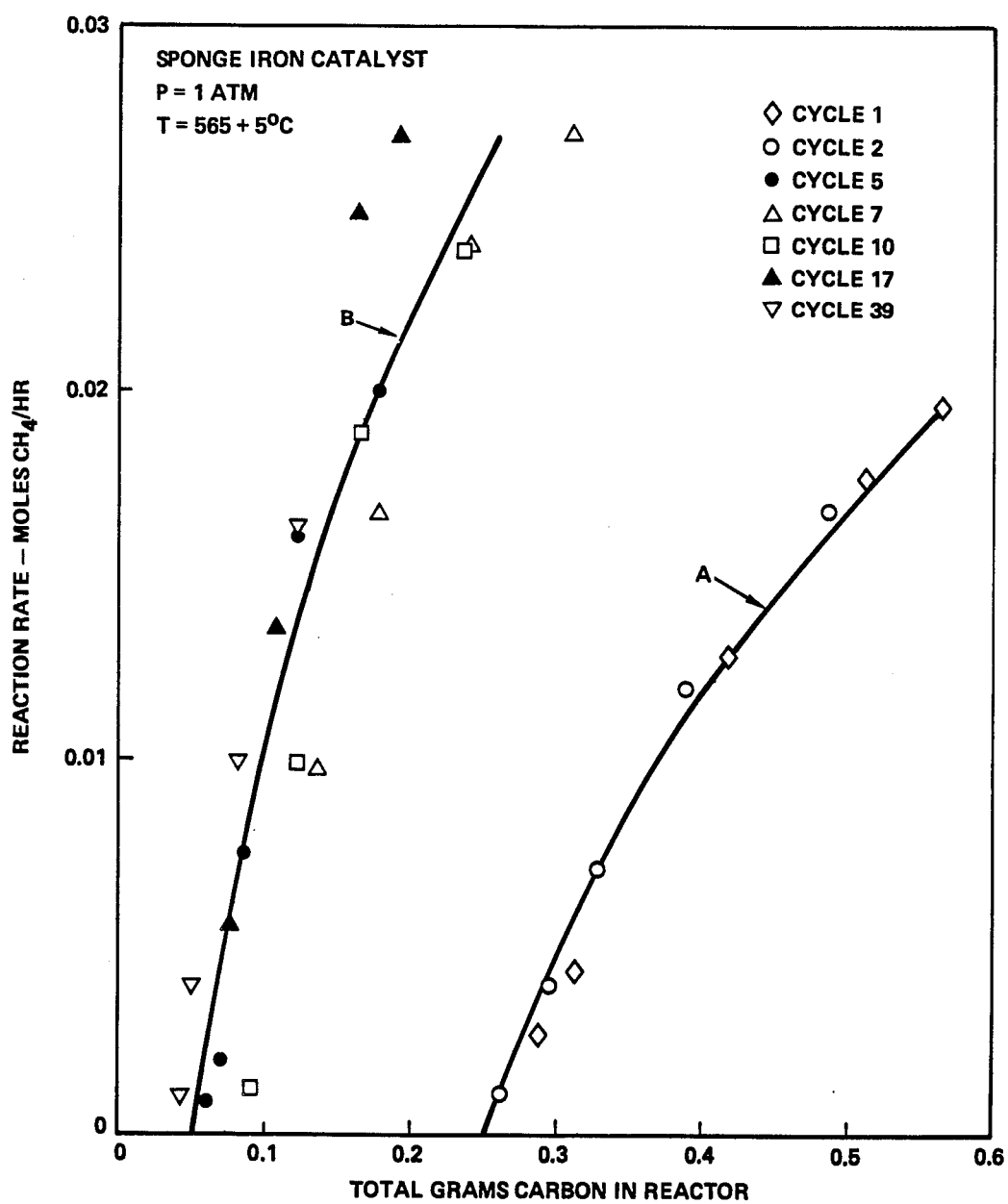
FIG. 10a is a graph showing the results of cycling one sample of carbonaceous material 39 times between carbon deposition by disproportionation and hydrogenation.

Whatever the reason for increased activity with cycling, the effect is dramatically shown in FIG. 10a, which summarizes the results of cycling one sample of carbonaceous material 39 times between carbon deposition by disproportionation to enhance the carbon-to-iron ratio of the material and hydrogenation to deplete the carbon content of the material. One gram of 40–60 mesh sponge iron was used as the bulk metal initiator, pure hydrogen was used for the hydrogenation cycles, and a mixture of 80% CO and 20% $H_2$ was used for the carbon deposition cycles. In FIG. 10a the hydrogenation rate is plotted against the instantaneous amount of carbon present in the reactor. It is apparent from FIG. 10a that major changes occur during cycling. Curve A of FIG. 10a shows the first two cycles of hydrogenation. During these two cycles, about 45% of the originally deposited carbonaceous material (0.25 grams) has little reactivity in comparison with the remainder of the carbonaceous material, since the curve A extrapolates to zero at about 0.25 grams. On the other hand, as illustrated by curve B, as cycling continues the amount of low reactivity carbonaceous material remaining in the reactor shows no indication of increasing, and in fact decreases dramatically. This indicates that the low activity carbon has become activated through cycling, probably due to increased dispersion of the active iron. Note also that the slope of curve B is greater than curve A, showing that the specific methanation rate increases as cycling continues.

Figure 10B:
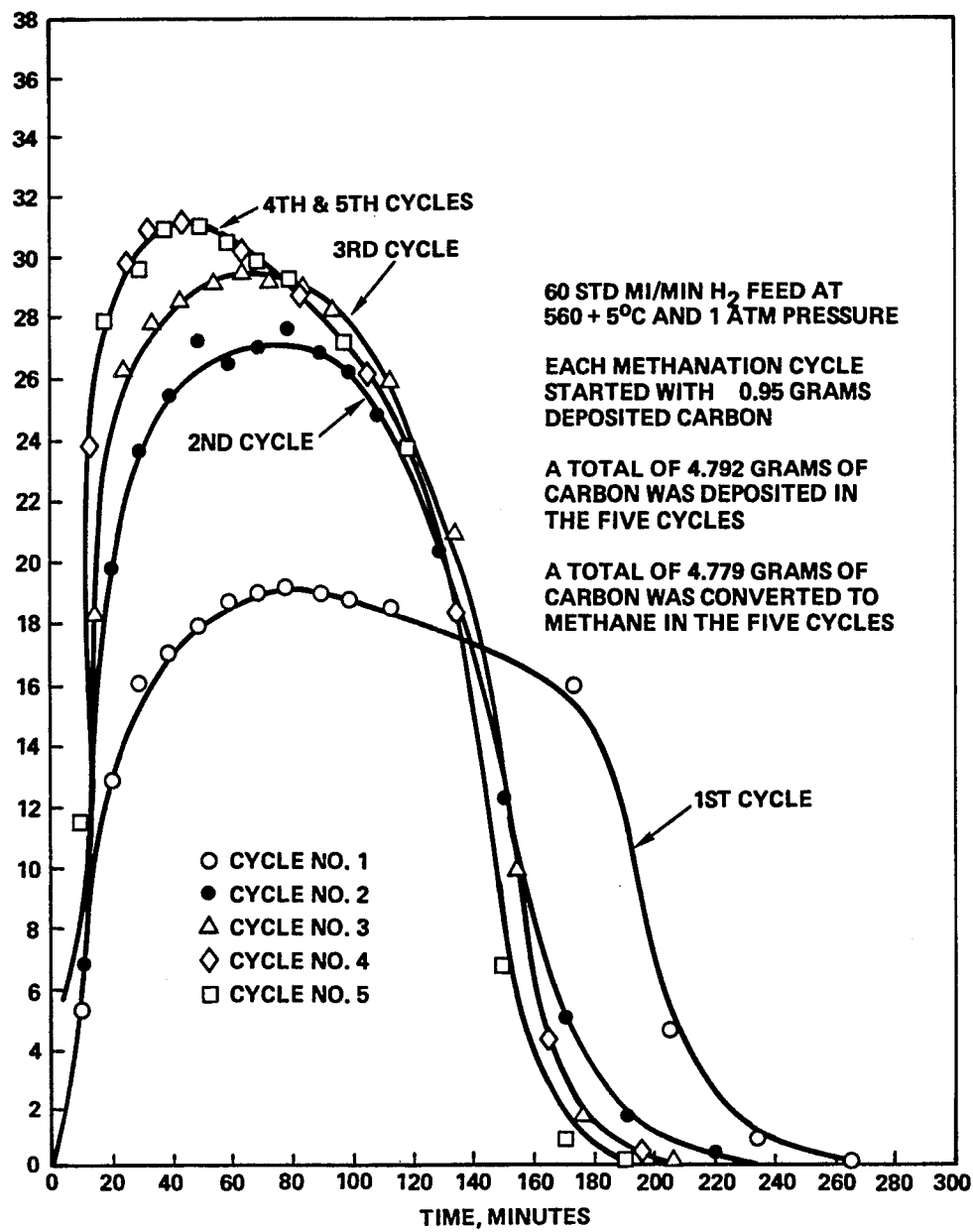
FIG. 10b is a graph showing the results of 5 cycles of methanation of carbonaceous material on a single sample of sponge iron catalyst at atmospheric pressure and 560° C.

FIG. 10b presents a graph showing the results of five cycles of methanation of our carbonaceous material on a single sample of sponge iron catalyst at atmospheric pressure and 560° C. In each cycle an identical amount (0.95 grams) of carbonaceous material was deposited on the catalyst prior to hydrogenation. The results show that the catalyst improves with cycling and that essentially all deposited carbonaceous material is converted to methane. In the five cycles a total of 4.792 grams of carbon were deposited and 4.779 or 99.7% were converted to methane. It is important to note from this FIG. 10b that the peak methane concentrations in the product gas closely approximate the maximum methane concentration allowable (33% $CH_4$) at 560° C. under equilibrium conditions even though gas contact times were less than 30 seconds. Methane concentrations in the product gas remain high until most of the carbon in the reactor has been gasified.

We have separated the enhanced material from the bulk metal initiator after the hydrogenation step and found that the enhanced material has the same general physical appearance as the material initially prepared, but the X-ray identification indicates that, where the ferrous group metal component is iron, the iron is alpha-iron rather than carbidic iron. As the material undergoes cyclic treatment, between carbon-rich and carbon-lean states, its composition may vary approximately as follows without adversely affecting its reactivity with hydrogen:

|  | % by weight |
| --- | --- |
| Partially graphitized carbon | 30–99.5 |
| Ferrous metal component | 0.5–70.0 |
| Hydrogen | 0.1–3.0 |

Moreover, the composition of the material may vary approximately as follows:

|  | % By weight |
| --- | --- |
| Partially graphitized carbon | 65–99.5 |
| Ferrous metal component | .5–35 |
| Hydrogen | .2–3.0 |

Typically, the cycled carbonaceous material contains from about 0.1 to about 3.0% by weight hydrogen. This hydrogen is strongly associated with the carbon. When we heat this cycled material in a nitrogen gas stream from about 200° C. to about 950° C., and analyze the carrier stream for desorbed gases, we find principally hydrogen. The hydrogen thus removed from our carbonaceous material is more than fifty thousand times the quantity we can dissolve in alpha-iron. Moreover, more than two-thirds of the hydrogen released during such runs comes off at temperatures above 700° C.

Again, it is emphasized that when we speak of weight percentages, we are speaking of our carbonaceous material after it has been separated from the bulk metal initiator.

Fisher-Tropsch Catalyst

We have found that the carbonaceous materials, particularly those containing ferrous group metal alloy nodules, are active catalysts for the conversion of hydrogen-carbon monoxide gas mixtures to hydrocarbons at elevated temperatures such as, for example, 350° C.–500° C. This classical Fisher-Tropsch reaction is illustrated as follows:

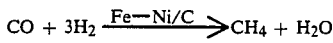

Since water is formed, the reaction between the carbon in the material and hydrogen is suppressed. The alloy nodules, for example iron-nickel alloy, is highly dispersed and acts as the catalyst.

EXAMPLES OF CARBONACEOUS MATERIAL

The following examples illustrate how to make carbonaceous materials, how these materials react with hydrogen to form methane, and how the materials act as a Fisher-Tropsch catalyst. Examples 1 through 4 show how some of the carbonaceous materials of our invention were prepared. Example 4 shows the methanation rates for several different ferrous group metal catalysts of our invention. Example 5 shows the unexpectedly good thermal stability of our catalytic materials. Example 6 shows how to make a carbonaceous material supported on alumina. Example 7 shows the activity of one of our carbon supported metal alloy catalysts used to make methane by the reaction of hydrogen and carbon monoxide.

Example 1

Carbon was deposited on one-eighth inch preoxidized, mild steel balls (5 grams) by decomposition of carbon monoxide at 550° C. from a carbon monoxide and hydrogen gas mixture in a tube furnace. The flow rate of the carbon monoxide was 100 milliliters (ml) per minute and the flow rate of the hydrogen was 20 ml per minute. After about 4 hours, 2.7 grams of the carbonaceous material containing 3.7% by weight of iron was separated from the steel balls, and 0.27 grams of the separated carbonaceous material was also exposed to the same carbon monoxide and hydrogen gas mixture at 500° C. and 1 atmosphere pressure. It was found that the carbon deposition rate was 8.8 grams of carbon per hour per gram of dispersed iron in the carbonaceous material present. This carbonaceous material had a methanation rate of 0.52 moles of methane formed per hour per mole of carbon. Carbon was again deposited on the hydrogenated material using the same carbon monoxide-hydrogen gas mixture and contacting the material at 500° C. at one atmosphere. The carbon deposition rate was 39.4 grams of carbon per hour per gram of dispersed iron. Cycling as above between the carbon monoxide disproportionation reaction to deposit carbon and thereafter hydrogenating the resulting carbonaceous material to remove most of the carbon was continued for several cycles. The result of all the cycles is summarized in Table II below.

TABLE II

| CYCLE NO. | CARBON DEPOSITION RATE (Grams/Hr/Gram of Dispersed Iron) | METHANATION RATE (Moles/Hr/Mole of Carbon) |
|---|---|---|
| 1-C* | 8.8 | |
| 1-H** | | 0.52 |
| 2-C | 39.4 | |
| 2-H | | 0.53 |
| 3-C | 47.8 | |
| 3-H | | 1.12 |
| 4-C | 41.5 | |
| 4-H | | 1.33 |

*Denotes carbon deposition
**Denotes hydrogenation
The twice-cycled material has a carbon deposition rate well in excess of 10 grams of carbon deposited per hour per gram of dispersed iron present. While the first cycled material had a relatively low carbon deposition rate, after this material was subjected to several more cycles of carbon deposition and methanation, both its carbon deposition and methanation rates increased substantially.

Example 2

Six hundred grams of Mesabi Range Iron ore (hematite type iron ore containing 55.3% Fe, 8.1% silica, 0.8% alumina) of particle size 60 to 150 mesh and bulk density 1.91 g/cm$^3$ was placed in a stainless steel pressure resistant verticle tube reactor having an inner diameter of 1.5 inches and a height of about 8 feet. The ore was reduced by a hydrogen gas stream contacting the iron ore at a space velocity of 2300 volumes of gas per volume of iron ore per hour. The reduced ore was subjected to a series of carbon deposition/methanation cycles. Carbon deposition was performed using nitrogen/carbon monoxide/hydrogen gas mixtures of different compositions, and the methanation was performed using pure hydrogen. The volumes of gases entering into the reactor and exiting after cooling the reactor to room temperature were measured with flow indicators and wet test meter, and the composition of gases was determined by gas chromatography. The conditions and results of several cycles are shown on the following Table III.

TABLE III

| | CARBON DEPOSITION | | | | | | | |
|---|---|---|---|---|---|---|---|---|
| | Gas Composition (%) | | | Av. Temp | Pressure atm | Av. Residence Time | Time | Atomic C:Fe After |
| Cycle | N$_2$ | H$_2$ | CO | °C. | abs | Seconds | Minutes | Carburetion |
| A | 46.6 | 8.1 | 45.3 | 456 | 6.1 | 1.9 | 65 | 1.29 |
| B | 42.5 | 6.9 | 50.6 | 440 | 3.4 | 1.7 | 75 | 0.88 |
| C | 44.2 | 6.9 | 48.9 | 435 | 3.5 | 1.6 | 90 | 0.80 |
| D | 44.2 | 7.4 | 48.4 | 416 | 4.7 | 1.8 | 110 | 1.12 |

| | METHANATION | | | | |
|---|---|---|---|---|---|
| Cycle | Temp. °C.* | Pressure atm abs | Av. Gas Residence Time, Seconds | Time Minutes | CH$_4$ in Product Gases (%) Maximum Attained | Atomic Ratio C:Fe After Methanation |
| A | 540–673 | 6.8 | 4.9 | 174 | 53.5 | 0.08 |
| B | 500–700 | 11.6 | 9.1 | 120 | 63.0 | 0.04 |
| C | 500–672 | 11.6 | 11.0 | 140 | 62.0 | 0.01 |
| D | 500–635 | 13.6 | 15.0 | 165 | 70.0 | 0.15 |

*Reaction was highly exothermic and the temperature was held under control only by adjustment of hydrogen flow.

Example 3

A 2.88 gram sample of iron-nickel alloy containing about 50 percent by weight of each of these two metals was oxidized at 982° C. for 10 minutes in a muffle furnace. The oxidized alloy was then carburized at 500° C. using a mixture of gases comprising 85 percent by volume carbon monoxide and flow rate 15 percent by volume hydrogen flowing at the rate of 200 milliliters per minute for 9.33 hours. After separating the carbonaceous material from the bulk alloy, we found that the elemental analysis of the resulting carbonaceous material was: Carbon: 98.06%, iron: 0.54%; nickel: 0.53% and hydrogen: 0.16%. The separated carbonaceous material was then subjected to a series of three methanation/carburization cycles. The conditions and results of these cycles are set forth in the following Table IV. The data in Table IV established that both the carbon deposition rates and the methanation rates improved with cycling of the material between carbon deposition and methanation.

TABLE IV

| CYCLE # | CARBON DEPOSITION RATE (Grams/Hr/Gram Dispersed Iron) | METHANATION RATE (Moles/Hr/Mole of Carbon) |
| --- | --- | --- |
| 1-H** | | 0.10 |
| 1-C* | 35.2 | |
| 2-H | | 0.12 |
| 2-C | 38.8 | |
| 3-H | | 0.20 |
| 3-C | 45.3 | |

*Denotes Carbon Deposition
**Denotes Hydrogenation

Example 4

Following the process of our invention, we prepared samples of carbonaceous materials from the disproportionation of carbon monoxide over preoxidized plates or buttons of iron, nickel, cobalt, and an iron-nickel alloy containing about 50% iron and about 50% nickel. In each sample, the fibrous carbonaceous material formed was separated from the bulk metal and exposed, at 500° C. and 1 atmosphere pressure, to a stream of dry hydrogen flowing at a rate of about 2 moles of hydrogen per hour per mole of the carbon present. The specific rates of methane formation for each of the samples is shown in Table V below.

TABLE V

| CO DISPROPORTIONATION INITIATOR | SPECIFIC RATE OF METHANE FORMATION OF FIBERS SEPARATED FROM BULK METAL IN MOLES/HOUR/MOLE CARBON |
| --- | --- |
| IRON | 0.10 |
| NICKEL | 0.19 |
| COBALT | 0.34 |
| IRON/NICKEL ALLOY | 0.10 |

Example 5

Ten grams of preoxidized carbon steel spheres measuring one-eighth inch in diameter were placed in an alumina boat which was then suspended in the center of a ceramic reactor tube. A mixture of 100 ml/min of carbon monoxide and 20 ml/min of hydrogen was passed over the spheres at 510° C. and atmospheric pressure for five hours. A total of 1.94 grams of carbon was deposited. The deposited carbonaceous material was carefully separated from the carbon steel spheres, and found to contain 2.08% iron. Of the separated material, 0.992 gram was placed in an alumina boat and returned to the reactor. A mixture of 100 ml/min of carbon monoxide and 20 ml/min of hydrogen was passed over the 0.992 gram sample at 408° C. for 2 hours. An estimated additional 0.2 grams of carbon was deposited as determined by measuring the carbon dioxide concentration of the effluent gas stream. Next, a gas stream of pure hydrogen (110 ml/min) was passed over this modified sample at a temperature of 560° C. Methane began to form and the hydrogenation was continued until approximately 0.2 grams of carbon were gasified, as determined by measuring the methane concentration and flow rate of the effluent gases. The average methanation rate was 0.20 mole $CH_4$/hr/mole of carbon. The gas stream flowing over the carbonaceous sample was then changed from hydrogen to pure nitrogen (40 ml/min) and the carbonaceous material was slowly heated to 865° C. The sample was held at 865° C. for about one hour and then cooled in flowing nitrogen to 560° C. At 560° C., the gas stream was again changed to pure hydrogen, flowing at a rate of 110 ml/min to effect methanation. Methanation continued until an additional 0.2 gram of carbon was gasified. The average methanation rate after the high temperature thermal exposure was 0.26 moles $CH_4$/hr/mole carbon. The cycle of high temperature (865° C.) thermal exposure to flowing nitrogen followed by hydrogenation at 560° C. was repeated. The average methanation rate was again determined and found to be 0.26 mole $CH_4$/hr/mole of carbon. Apparently, this short term exposure of carbonaceous material to high temperature does not impair its reactivity with hydrogen. Nor did the high temperature exposure impair its catalytic activity in the direct conversion of carbon monoxide and hydrogen to methane. After the same thermal cycles, the remaining carbonaceous material was exposed to a mixture of 110 ml/min of hydrogen and 30 ml/min of carbon monoxide at 450° C. Methane found in the effluent gas formed at an average rate of 0.24 mole/hr/mole carbon.

Example 6

A 1.7812 gram sample of a commercial, alumina supported iron catalyst (Harshaw FeO30P, 14% Fe on alumina, 105 m²/gram surface area) was used as the bulk metal initiator. The sample was placed in an alumina boat in a tube reactor and a mixture of 120 std ml/min of carbon monoxide and 30 std ml/min of hydrogen passed over the sample at 450° C. and one atmosphere pressure for three hours. An amount of 0.326 gram of carbonaceous material was deposited on the initiator. The resulting material in the boat reactor was next exposed to a stream of hydrogen passed over the sample at a flow rate of 60 std ml/min, at 560° C. and 1 atmosphere pressure. Over a one hour period, the average methane concentration in the effluent gas was 19.4% $CH_4$ and 0.297 gram of carbon was gasified. The average methanation rate was 1.68 moles $CH_4$/hr/mole carbon measured at 550° C., one atmosphere pressure, and a hydrogen flow rate of 2 moles of hydrogen per hour per mole of carbon present.

EXAMPLE 7

Two and eighty-eight hundredths grams of an iron-nickel alloy button (prepared by arc melting) containing 50.66% by weight iron was used as the bulk metal initiator for depositing carbon from a gas stream containing 85% by volume carbon monoxide and 15% by volume hydrogen. On this preoxidized button a total of 5.38 grams of carbon was deposited at 500° C. and one atmosphere pressure and the carbonaceous material carefully separated from the bulk alloy button. The resulting separated material contained 98.06% carbon, 0.54% iron, 0.53% nickel and 0.16% hydrogen on a weight basis. One gram of the above prepared and separated carbonaceous material containing the dispersed iron-nickel alloy (1.06%) was used as a catalyst for the reaction of 50 ml/min of a 3:1 $H_2$/CO by volume gas mixture at 500° C. and one atmosphere pressure. Reaction was carried out in a small tubular reactor and product concentration and inlet feeds monitored by frequent gas chromatograph analysis. The steady state product contained 7.1% $CH_4$ and 5.9% $CO_2$ at 500° C. A specific rate of conversion of the CO/$H_2$ mixture to methane of 51 moles $CH_4$/hr/mole active metal was achieved. This was very high considering that there was only about ten milligrams of active metal catalyst present.

All the carbonaceous material prepared in the above examples had a reactivity with hydrogen of at least 0.1 mole of methane formed per hour per mole of carbon present when the carbon is contacted with hydrogen at a temperature of 550° C., one atmosphere pressure, and a minimum hydrogen feed rate of 2 moles of hydrogen per hour per mole of carbon present.

PROCESS FOR MAKING HIGH BTU GAS

General

Our invention also includes a process for producing a high Btu gas from coal or other carbonaceous fuels through the vehicle of the carbonaceous material. Our process produces pipeline quality gas because the following requirements can be satisfied:

(i) At the desired operating temperature and pressure, high concentrations of methane (70–80% $CH_4$) must be thermodynamically allowable.

(ii) At temperatures and pressures where equilibrium allows high concentrations of methane to exist, these concentrations must be kinetically achievable in a commercially reasonable residence time (about 30 seconds).

(iii) Essentially all of the deposited carbonaceous material must be highly reactive with hydrogen. If any significant fraction of the carbonaceous material is nonreactive, then a continually increasing build-up of "dead" carbon will occur, essentially destroying the cyclic nature of the process.

(iv) The carbonaceous material must be capable of many cycles from a carbon-lean state to a carbon-rich state without loss of activity.

Figure 11:
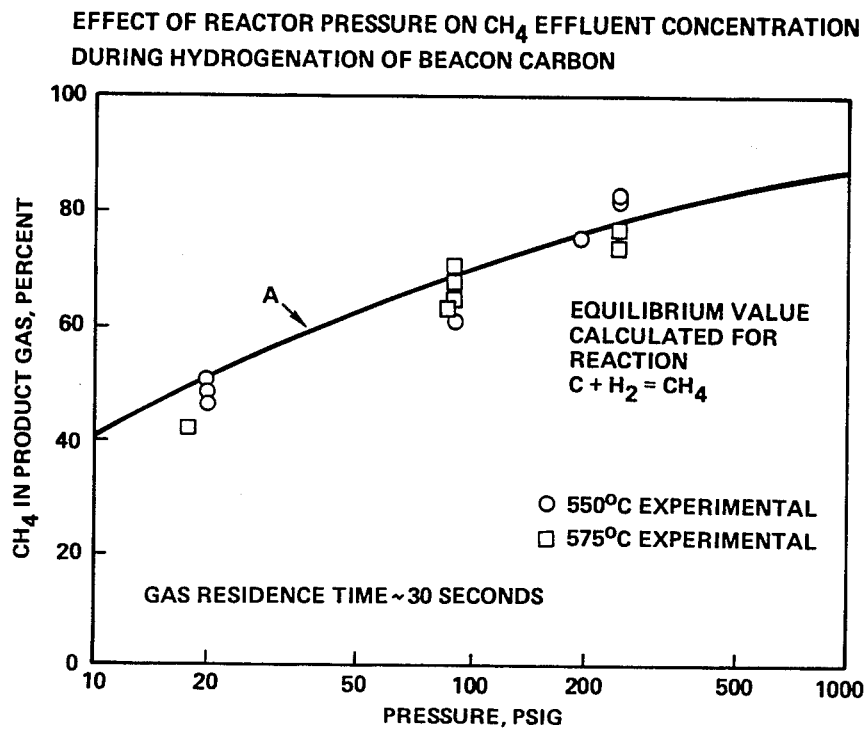
FIG. 11 shows the effect of reactor pressure on $CH_4$ effluent concentration during hydrogenation of Beacon carbon.
Figure 12:
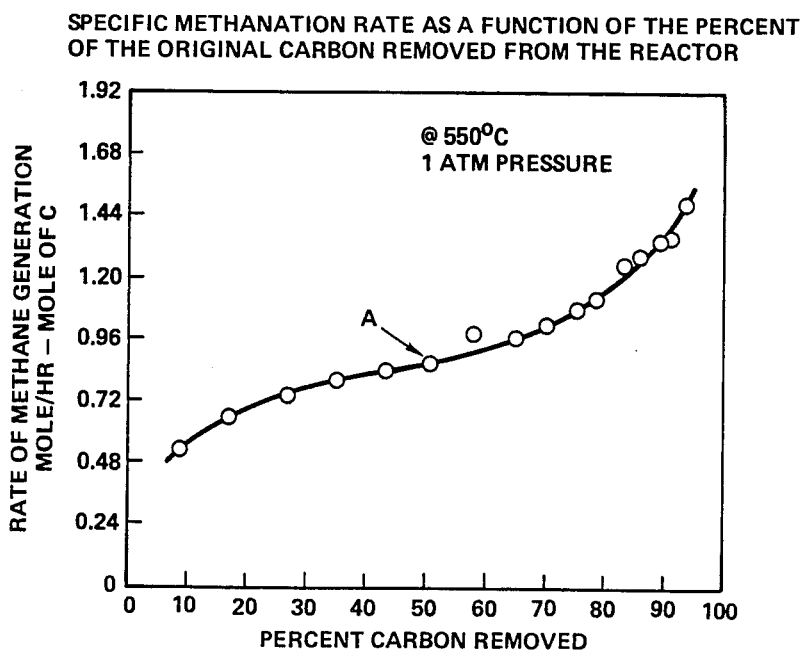
FIG. 12 shows the specific methanation rate as a function of the percent of the original carbon removal from the reactor.

FIGS. 11 and 12 illustrate that we can meet the first three requirements. In FIG. 11 it is shown that experimental data at 550°–575° C. closely follows the calculated equilibrium concentration of methane (shown as curve A) as a function of operating pressure for commercially viable gas residence times of about 30 seconds. In curve A of FIG. 12 it is shown that essentially all the material is reactive and that the specific methanation rate increases gradually as the carbon is hydrogenated and is still increasing even after 93% of the original carbon in the batch reactor was gasified. FIGS. 13 and 14 illustrate the fourth basic requirement. A single batch of iron catalyst was cycled between deposition of carbon from a simulated producer gas and hydrogenation of that carbon to produce methane. A total of 63 cycles was run. The cyclic testing involved a wide range of temperature (300°–650° C.), pressures (20–250 psig) and space velocities. The activity of the material at the end of cycling was greater than at the beginning. Hydrogenation of deposited carbonaceous material in Cycle No. 22 is shown in FIGS. 13 and 14. A peak methane concentration of 83% was obtained at 550° C., 250 psig and 30 seconds gas residence time. A level exceeding about 65% methane concentration was maintained until almost all of the carbon in the material was converted to methane.

In our process methane can be made without the need to use pure oxygen or to remove nitrogen, carbon dioxide, or other inert gases from the feed stream. According to our process, the carbon monoxide and hydrogen are extracted from the feed stream by forming the carbonaceous material on the bulk metal initiator. A hydrogen-containing gas is then contacted with the carbonaceous material at a temperature, pressure, and space velocity that produces a methane containing product gas including at least 20% by volume methane. Because the carbonaceous material is so highly reactive with hydrogen, the residence time of the hydrogen in contact with the carbonaceous material may be very short. We have found that the carbonaceous material requires little residence time with hydrogen to produce a gas containing as high as 75% by volume or greater methane. For example, the residence time may vary from one second to 100 seconds to produce such a methane-rich gas. The preferred hydrogen residence time is from about five seconds to about 60 seconds. The pressure may range between about one and about 100 atmosphers, preferably 1–25 atmospheres. The desirable minimum temperature at which methanation is conducted is 350° C. The preferred range is from about 450° C. to about 750° C.

Figure 15:
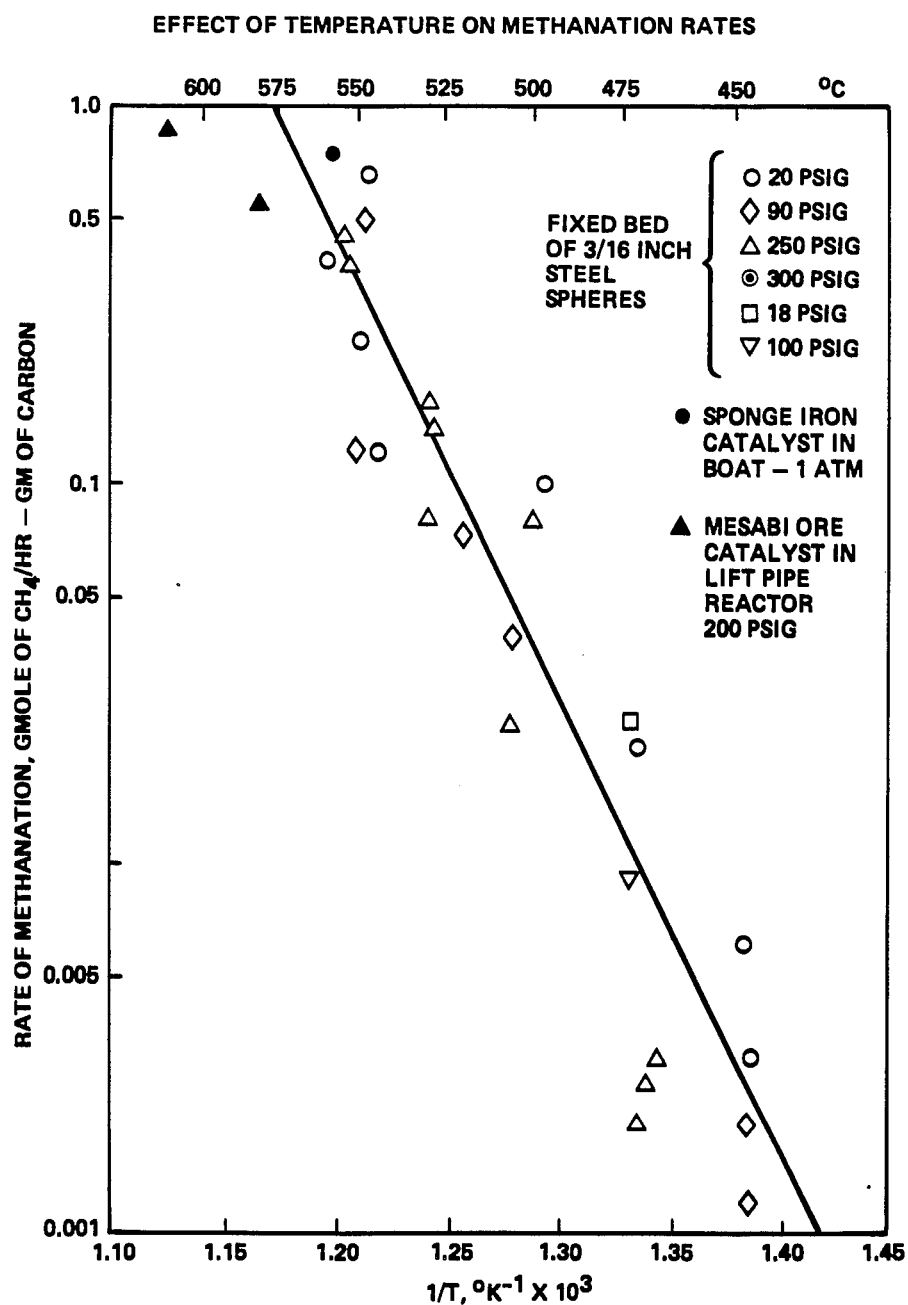
FIG. 15 shows the effect of temperature on methanation rates.

The methanation rate is very sensitive to temperature, as illustrated by FIG. 15. FIG. 15 presents a log plot of differential methanation rates (at low $CH_4$ concentrations) vs the reciprocal of the absolute temperature (Arrhenius plot) for the data obtained with carbonaceous material produced from three different types of bulk metal initiators (3/16" steel spheres, powdered iron, and pre-reduced Mesabi iron ore), at pressure from 20–300 psig. It is apparent from this Figure that the specific methanation rate (at low $CH_4$ concentration in the reactor) is exponentially dependent on temperature which is the dominant variable. From 575° C. to 500° C. the specific methanation rate decreases by a factor of twenty.

In the process of our invention almost any carbon monoxide-containing gas can be used to produce a high Btu, methane containing gas. Specific gases which may be used in our process are those gases produced by gasifying coal using air or a mixture of air and steam to produce a low Btu producer gas of from about 70–150 Btu per cubic feet. For example, coal may be burned in-situ (i.e., without removing the coal from its natural site) to produce a gas having about 100 Btu per cubic foot. As used here, a producer gas is one which contains carbon monoxide, hydrogen, nitrogen, and carbon dioxide. Preferably, the coal is burned in a mixture of air and steam to provide a producer gas rich in carbon monoxide and hydrogen. For example, producer gases normally will contain, on a dry basis, from about 15% to about 30% carbon monoxide, from about 5% to about 30% hydrogen, from about 40% to about 60% nitrogen, and from about 2% to about 10% carbon dioxide. All of these carbon-monoxide containing gases may be converted to a methane-rich gas similar to natural gas and having a heat content of from 500 to as much as 1000 Btu per cubic feet.

In general, producer gases will also contain water and small amounts of other gases such as methane, hydrogen sulfide, carbonyl sulfide, and the like. For operation at atmospheric pressure, the water content should be reduced below about 6% by volume; the sulfur content below about 10 parts per million. If the carbon monoxide feed gas contains hydrogen, the molar ratio of carbon monoxide to hydrogen should be greater than about 1:2, preferably greater than 1:1. The preferred molar ratio of carbon monoxide to hydrogen is between about 1:1 to about 100:1. When the feed gas contains carbon dioxide, preferably the molar ratio of carbon monoxide to carbon dioxide is high. In general, the carbon monoxide to carbon dioxide molar ratio should be 1:1 or greater, preferably greater than 2:1-3:1. However, carbon deposition proceeds at acceptable rates even when the ratio of carbon dioxide to carbon monoxide is as high as 2:1.

We have found that the initial feed gas containing solid carbonaceous material as an intermediate. A methane-rich gas is subsequently produced by simply contacting the carbonaceous material with hydrogen. This solid carbonaceous material need not be immediately reacted with hydrogen, since it retains its reactivity for a considerable period of time. For example, we have stored one sample for five days and reacted the sample with hydrogen and formed methane at the same high rates as freshly prepared carbonaceous material. This enables energy to be stored until needed.

Our experiments demonstrate that substantially all the carbon monoxide and hydrogen in the producer gas will be converted to the carbonaceous material in a short residence time. This is especially true when a relatively high surface area iron catalyst is used in a fluid bed or entrained bed. Table VII shows one set of operating conditions where 77% total utilization of combustibles was achieved with only two seconds of gas residence time.

TABLE VII
EXAMPLE OF UTILIZATION OF PRODUCER GAS DURING CARBON DEPOSITION

| Feed Conditions to Fluid Bed Reactor | | Pressure - 70 Psia | |
|---|---|---|---|
| CO In | 3374 ml/min; 43 mole % | Gas Residence Time | 2~Seconds |
| $H_2$ In | 435 ml/min; 6 mole % | Temperature | 450° C. |
| $N_2$* In | 3974 ml/min; 51 mole % | Catalyst | Mesabi Ore |
| | 7783 ml/min Total Flow In | | |
| Product Gases Out of Reactor | | | |
| CO Out | 384 ml/min; 6.6 mole % | Carbon Deposition Rate | .9 Grams/Min |
| $H_2$ Out | 354 ml/min; 6.1 mole % | Carbon Monoxide Conversion | 88.6% |
| $N_2$* Out | 3905 ml/min; 67.5 mole % | Hydrogen Conversion | 18.6% |
| $CO_2$ Out | 1092 ml/min; 18.9 mole % | % Utilization of Combustibles | 77% |
| $CH_4$ Out | 47 ml/min; 0.8 mole % | | |
| | 5782 ml/min Total Flow Out | | |

*$N_2$ in is determined by orifice meters and $N_2$ out by wet test meters and chromatographic analysis. Therefore, $N_2$ in and out provides a consistency check.

carbon monoxide should not contain appreciable amounts of sulfur. Specifically, the carbon monoxide feed gas should not contain more than about 10, preferably not more than 1, parts per million of sulfur calculated as hydrogen sulfide. When required, sulfur removal may be accomplished by well-known methods; for example, amine systems, or by contacting the feed gas with an aqueous solution of an alkali metal or alkaline earth metal carbonate such as hot potassium carbonate. In addition to conventional methods of removing hydrogen sulfide from feed gases, we have also found that hydrogen sulfide can be removed by passing the feed gas over the carbonaceous material or a mixture of the carbonaceous material and the bulk metal initiator. When this is done, we believe, the ferrous metal reacts with the sulfur, present predominantly as hydrogen sulfide, to form metal sulfides within the material. This reaction deactivates the carbonaceous material. Therefore, if this method is used to remove the sulfur from the feed gas, the sulfur containing carbonaceous material cannot be used to produce methane.

Since our invention is able to use gases containing nitrogen in relatively large amounts (for example, nitrogen may be present in amounts as great as 70% by volume or greater), it is not necessary to form the carbon monoxide containing gas in a nitrogen free atmosphere. That is, air may be used to burn coal rather than pure oxygen. What makes our process economically attractive is that the combustion portion of the feed stream, principally the carbon monoxide, is extracted or separated at low cost from the inert or noncombustible portion of the feed stream through the formation of the According to one embodiment of our invention, carbonaceous material (ordinarily mixed with the bulk metal initiator) is cycled between two reaction zones, one in which the carbonaceous material is contacted with the producer gas and one in which the material is contacted with the hydrogen-rich gas to make methane. Thus, the material undergoes a transition between a carbon-rich state and a carbon-lean state. The material being fed to the zone producing methane is rich in carbon. Some of the carbon is stripped (for example, 15 weight percent) from this material during the formation of methane to produce the carbon-lean material which is transferred to the other zone where it is again enriched with carbon by contact with the producer gas. The carbon-lean material will, in the first cycle, contain between about 5 to 70 weight percent of the dispersed ferrous metal component, about 95 to 30 weight percent carbon, and about 0.1 to 3 weight percent hydrogen. The carbonaceous material may, however, remain in one zone and the gas streams flowing through such zones are alternated between producer gas and hydrogen-rich gas streams.

Sources of Hydrogen

We may obtain hydrogen from any suitable source; however, two known processes for providing hydrogen are particularly useful in the production of methane according to our invention. These two processes are the steam-iron process and gasification/shift conversion process.

In utilizing the steam-iron process, the producer gas is used to reduce $Fe_2O_3$ to Fe, $Fe_3C$ or FeO, which are subsequently reacted with steam to make hydrogen. The producer gas may be used initially as the reducing agent for the $Fe_2O_3$ or after it is partially depleted as a result of forming the carbonaceous material. The partially depleted producer gas may contain about one-half as much hydrogen as the producer gas initially contacting the $Fe_2O_3$. When the steam-iron process is used, there is no need for an oxygen generation plant.

The second process, gasification of fossil fuel plus shift conversion, is illustrated by the following equations:

$$\text{Coal or Char} + H_2O + O_2 \rightarrow CO + H_2 \quad (1)$$

$$CO + H_2 + H_2O \rightarrow CO_2 + 2H_2 \quad (2)$$

As depicted by equation 1, a mixture of oxygen and water vapor oxidizes coal or char to produce a synthesis gas of carbon monoxide and some hydrogen. Equation 2 illustrates the shift conversion by reacting the synthesis gas with additional steam to produce carbon dioxide and hydrogen. The carbon dioxide is then separated from the hydrogen which is used in the methanation step.

Production of Electricity

Our process also permits co-production of substantial quantities of electric power from the depleted producer gas or other gas used as a source of carbon monoxide. Thus, after the producer gas has been utilized to manufacture carbonaceous material and to make hydrogen by the steam-iron process, the depleted gases are preferably then burned in air to oxidize any remaining combustibles and the resulting gases are expanded through a gas turbine to recover their energy as electricity.

One of the major advantages of our process is that most of the waste heat generated becomes available at a very high top temperature, for example, in excess of 800° C., for efficient conversion to co-product electric power. The net result is that more of the low Btu producer gas is converted to high value energy products (electricity and methane-rich gas) than in conventional processes.

DETAILED DESCRIPTION OF THE PREFERRED EMBODIMENTS

Figure 8:
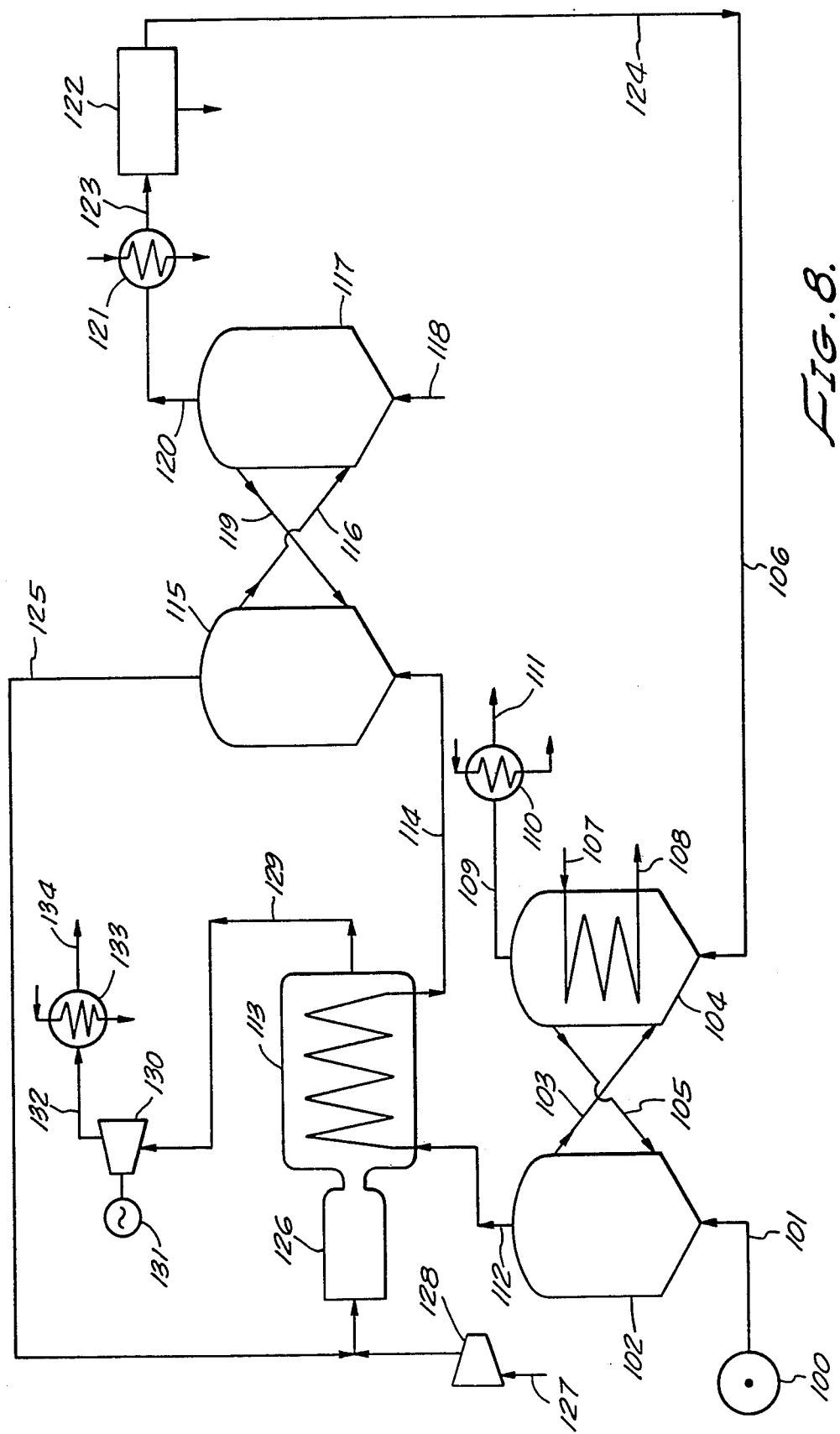
FIG. 8 schematically shows a fifth process for practicing the present invention

The best mode which we presently contemplate for practicing our invention is shown schematically in FIG. 8. In FIG. 8, desulphurized producer gas from source 100 is the feed stream. This gas may include, for example, 50 percent nitrogen, 25 percent carbon monoxide, 18 percent hydrogen, 6 percent carbon dioxide and one percent methane, on a dry basis. It sulphur content must be less than about 10 parts per million.

The cool, clean producer gas passes via line 101 to fluidized bed carbon deposition reactor 102, which contains carbon-lean solids including a ferrous metal such as iron. Exothermic carbon deposition occurs in reactor 102 by disproportionation of the carbon monoxide in the producer gas at a fluid bed temperature of about 650° C. and at a pressure in the range 150-250 pounds per square inch. The heat released in carbon deposition is taken up primarily as sensible heat in the partially depleted producer gas.

The carbonaceous material of our invention formed in reactor 102 passes through line 103 to methanator 104. There, at a temperature in the range of about 525° C. to about 700° 1 C., the carbon in the carbonaceous material reacts with dry hydrogen entering methanator 104 through line 106 to form methane. Because methanation is highly exothermic, and because lower temperatures favor the formation of methane in higher concentrations, methanation is effected in stages, with the solids and gases cooled between the stages. Depending on the desired product composition, one or more interstage coolers may be required. Here, cooling is effected with water entering methanator 104 through line 107 and exiting as steam through line 108.

The methane/hydrogen gas mixture leaves methanator 104 in line 109, passes through cooler 110, and emerges in line 111, ready for further processing.

The partially depleted producer gas from carbon deposition reactor 102 passes therefrom through line 112 to heat exchanger 113. There, the temperature of this gas is raised from about 670° C. to about 920° C., and the residual methane and steam in the gas converts in part to hydrogen and carbon monoxide. The partially depleted producer gas leaving heat exchanger 113 has a lower ratio of carbon monoxide to carbon dioxide than the feed gas from source 100, and contains principally nitrogen, carbon monoxide, hydrogen, water and carbon dioxide. Though lower, the $CO/CO_2$ ratio is sufficiently high to permit its use for reducing iron oxides.

The partially depleted producer gas leaves heat exchanger 113 and passes through line 114 to iron oxide reducer 115. There, the mixture reduces ferrous ferric oxide ($Fe_3O_4$) to ferrous oxide (FeO), and oxidizes carbon monoxide to carbon dioxide and hydrogen to water. The reduced iron oxides pass from reducer 115 via line 116 to hydrogen producing reactor 117. Steam enters reactor 117 through line 118 and reacts with the ferrous oxide to produce $Fe_3O_4$ and hydrogen. The $Fe_3O_4$ passes to reducer 115 through line 119. The wet hydrogen produced passes from reactor 117 via line 120, is cooled in condenser 121, and then passes through line 123 to separator 122. In separator 122, the water content of the hydrogen stream is reduced to less than about 1% by weight. Dry hydrogen emerges from separator 122 in line 124, and passes to methanator 104 through line 106.

The partially depleted producer gas entering reducer 115 passes therefrom in line 125 as a nearly depleted gas. However, the gas still contains useful residual energy. That energy is preferably utilized by burning the gas in furnace 126 with air from source 127. Compressor 128 raises the inlet air pressure in furnace 126 to the range of about 10–20 atm. The heat produced in furnace 126 is partially consumed in heat exchanger 113 to raise the temperature of partially depleted producer gas from reactor 102. The remaining heat in the gases from furnace 126 passes from heat exchanger 113 via line 129 to turbine 130, where the gases are expanded to produce electrical power at 131. The depleted gas exits turbine 130, is cooled in steam generator 133, and passes to the atmosphere via line 134.

This embodiment of our process has several outstanding advantages. First, a very high percentage of the cold gas heating value of the producer gases is utilized effectively in conversion to high value products, methane and electricity. Secondly, expensive oxygen is not required in this process. Third, the heat released in the methanation step and the remaining sensible heat in the depleted producer gas are available for use at high temperatures. As illustrated, the heat associated with deposition of carbon is taken up as sensible heat in the producer gas and ultimately becomes available for power generation at 800° C.-1100° C. The heat associated with the direct hydrogenation of carbon is available from 500° C. to about 700° C., which is much higher than the 300°-350° C. heat available from the staged conversion of three moles of $H_2$ and one mole of carbon monoxide to methane using conventional catalyst. The net result of the high temperature availability of waste heat is the production from a ton of coal of more high value product, methane and electric power, than in conventional processes.

Figure 4:
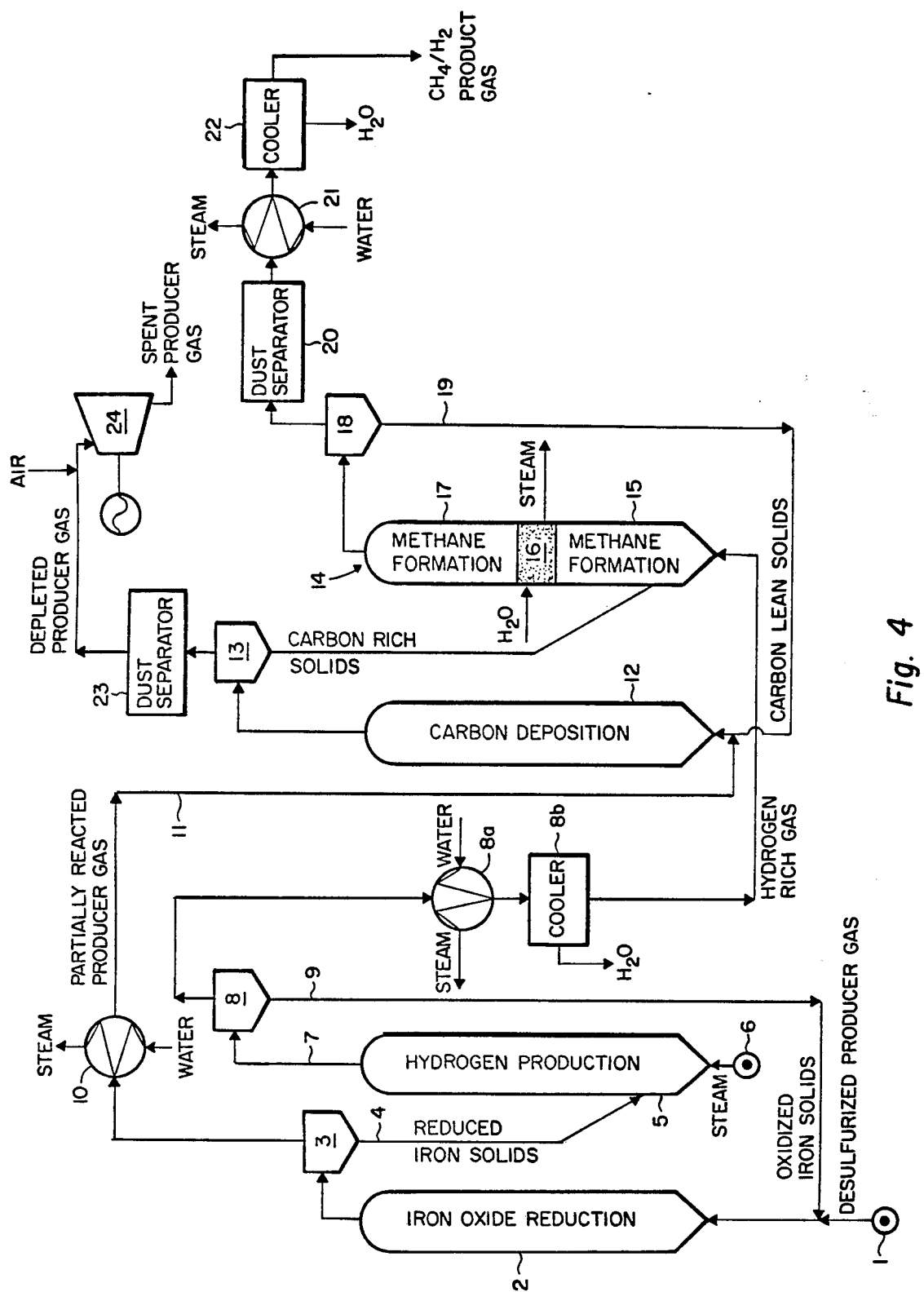
FIG. 4 schematically shows a first process for practicing the present invention.

Another embodiment of our process is shown schematically in FIG. 4. Desulfurized producer gas from source 1 is the feed stream. This gas, which may comprise, for example, 50% $N_2$, 25% CO, 18% $H_2$, 6% $CO_2$, and 1% $CH_4$ on a dry basis, may be derived from conventional gasification of coal with steam and air, "in-situ" gasification of coal, etc. The raw producer gas is desulfurized to below about 10 ppm of $H_2S$.

Desulfurized producer gas and, for example, oxidized iron solids such as a mixture of $Fe_2O_3$, $Fe_3O_4$, and FeO are contacted in a fast fluidized bed or entrained solid lift pipe type reactor 2 at temperatures from about 550°-850° C. and at pressures of 1-100 atm, preferably about 1-20 atm. Choice of temperature and pressure are dependent on the overall heat balance and the desired methane concentration of the product gas. Solid-gas contact is maintained for a sufficient time to cause partial reduction by the $H_2$ and CO in the producer gas of the iron oxides to reduced iron compounds such as FeO, Fe, and $Fe_3C$. The $H_2$ and CO content of the producer gas feed is partially, but not fully, consumed in the reduction of the iron oxides. We believe that the $H_2$ will be more fully utilized than the CO in this step of our process.

The entrained, reduced iron solids and partially reacted producer gas are next fed to a cyclone or similar device 3, where the reduced iron solids are separated from the partially reacted producer gas. The separated, reduced, iron solids are fed through line 4 to the bottom of a second lift pipe reactor 5 where they are contacted with steam from source 6 at temperatures of about 500°-800° C. and pressures of 1-101 atm. A hydrogen-rich gas is obtained from the reaction of the steam with the reduced iron solids. In addition to hydrogen and unreacted steam this gas will also contain some methane, carbon monoxide, and carbon dioxide.

The hydrogen-rich gas and entrained oxidized iron solids from the hydrogen production reactor 5 exit through line 7 and are next fed to a cyclone or similar device 8, which separates the solids from the gases. The oxidized iron solids are returned via line 9 to the first lift pipe reactor 2 to complete the solid circulation loop between reactors 2 and 5.

After separation of the solids, the partially reacted producer gas, which now may contain, for example, 15% CO, 6% , $H_2$, 16% $CO_2$, 1% $CH_4$, and 62% $N_2$ on a dry basis, is cooled in heat exchanger 10 generating process steam. This cooled gas is fed via line 11 to the bottom of the lift pipe carbon deposition reactor 12, where it contacts and entrains carbon-lean solids. The gas and solids are maintained in contact with each other for a sufficient length of time at temperatures of 300°-600° C. and pressures of 1-100 atm to cause carbon to deposit on the carbon-lean solids and enrich their carbon content. Carbon deposition occurs by disproportionation of the carbon monoxide content of the partially reacted producer gas and, to a lesser extent, by reaction of CO and $H_2$ or by the reduction of CO by other reducing agents present.

The entrained carbon-rich solids leaving the carbon deposition reactor 12 are separated from the now depleted producer gas in a cyclone or similar device 13 and fed to the bottom of a lift pipe methanation reactor 14, where they are entrained by the hydrogen-rich gas stream coming from the hydrogen production reactor 5 via heat exchanger 8a and cooler 8b. The entrained carbon-rich solids react with hydrogen in the first stage 15 of the methanation reactor 14 predominately by the direct reaction of carbon and hydrogen. This is an exothermic reaction and the solids and/or gases must be cooled between stages if high concentrations of methane are desired. Entrained solids and gases are cooled in an interstage cooler 16, and then further reacted in a second reactor stage 17 to produce additional methane. Depending on the desired ratio of $CH_4$ to $H_2$ in the product gas, operating pressures in the methanation reactors may vary from about one to about 100 atm, but preferably will be from about one to about 20 atm. Again, depending on the desired product, one or several stages of intercooling may be employed. Operating temperatures in the initial stages of the methanation reactor may go up as high as 700°-750° C., but lower temperatures must be held in the final methanation stages if a high $CH_4$ to $H_2$ ratio is desired.

The product gas and entrained carbon-lean solids leaving the methanation reactor 14 are primarily separated in cyclone 18. The carbon-lean solids are then recycled via line 19 to the carbon deposition reactor 12. The raw product gas still containing some entrained dust is further cleaned in a dust separation unit 20, which may be a magnetic separation device since most of the dust will be ferromagnetic. Sand filters or other types of dust cleaning operations may, however, be used. The dust free product gas is cooled in heat exchanger 21, producing process steam and further cooled and dried in cooler 22 to produce the final product gas.

The hot depleted producer gas leaving cyclone 13 is fed to a dust separator 23 which removes entrained dust not separated by the cyclone 13. The dust separator may be a magnetic separation device since the solids are ferromagnetic, or it may be a more conventional system such as a sand filter. The hot, dust free, depleted producer gas, still containing some $H_2$ and CO, is burned by the addition of excess air to yield a high temperature combustion gas product, containing $N_2$, $CO_2$, and $H_2O$. This hot gas is expanded through a gas turbine 24 to produce byproduct shaft work and/or electric power. Finally, the spent producer gas may be further cooled to produce additional process steam.

Two of the major advantages of the process depicted in FIG. 4 are (a) that separation of undesirable $N_2$ and $CO_2$ from $CH_4$ and $H_2$ product gas occurs through the relatively easy separation of solids and gases rather than the much more difficult separation of $N_2$ from $O_2$ as required in conventional technology, and (b) that the producer gas in this process is more fully utilized in conversion to a $CH_4/H_2$ product than in a conventional steam-iron process, since the producer gas is first partially used to reduce iron oxides (steam-iron process) and then more fully utilized to deposit reactant carbon.

Figure 5:
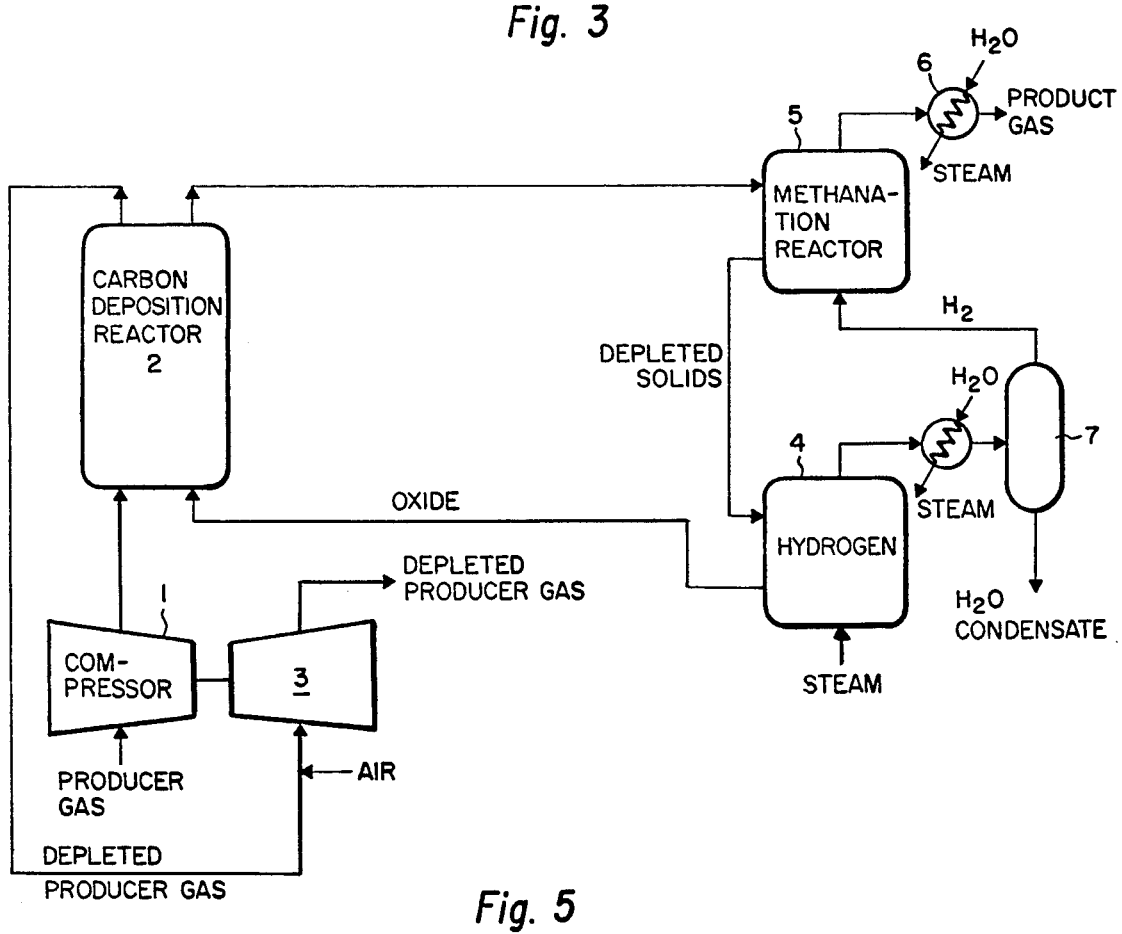
FIG. 5 schematically shows a second process for practicing the present invention.

A third way of practicing our invention is shown in FIG. 5. Here, producer gas is initially compressed to about 3 to 4 atmospheres in compressor 1 and fed into a carbon deposition/ferrous metal oxide, (e.g., iron oxide) reduction reactor 2 where it initially contacts iron oxides and reduces these oxides and simultaneously deposits carbonaceous material on the reduces oxides. The reactor 2 is maintained at a temperature of about 350°–500° C. and a pressure of about 3 to 4 atmospheres. In reactor 2, about 70% of the carbon monoxide and hydrogen in the producer gas reacts with the iron oxides to form reduced iron compounds and the carbonaceous material of this invention. The depleted producer gas, at a temperature of about 350°–500° C., is mixed with air and burned in combustion zone 3. This gas may be then passed directly to a compressor or an electric generator for expansion without passing through a waste heat boiler. However, the gas is preferably passed through a magnetic separator to remove any entrained dust.

The carbonaceous material, including the bulk iron, is circulated through fluidized stand pipes to a fluid bed methanation reactor 5 where it is contacted with hydrogen gas at temperatures of about 480°–535° C. and a pressure of about 3 to 4 atmospheres to form a methane-rich gas. The methane-rich gas is cooled in waste heat boilers 6 to produce process steam. The carbon depleted material from methanation reactor 5 is circulated via fluidized standpipes to the fluid bed hydrogen generation reactor 4 and contacted with steam at about 535°–650° C. and a pressure of from 3 to 4 atmospheres to produce wet hydrogen. The resulting iron oxides are recirculated back to the carbon deposition reactor 2. The wet hydrogen is cooled in cooler 7 to condense the water vapor and the dry hydrogen circulated to the methanation reactor 5.

Sulfur compounds such as $H_2S$, COS, and $CS_2$, if present in the producer gas, may be removed by contacting the gas with a portion of the carbonaceous material formed in carbon deposition reactor 2. Alternatively, the portion of the carbonaceous material which has been hydrogenated may be removed from the methanation reactor 5 and contacted with the producer gas to remove the sulfur compounds.

Figure 6:
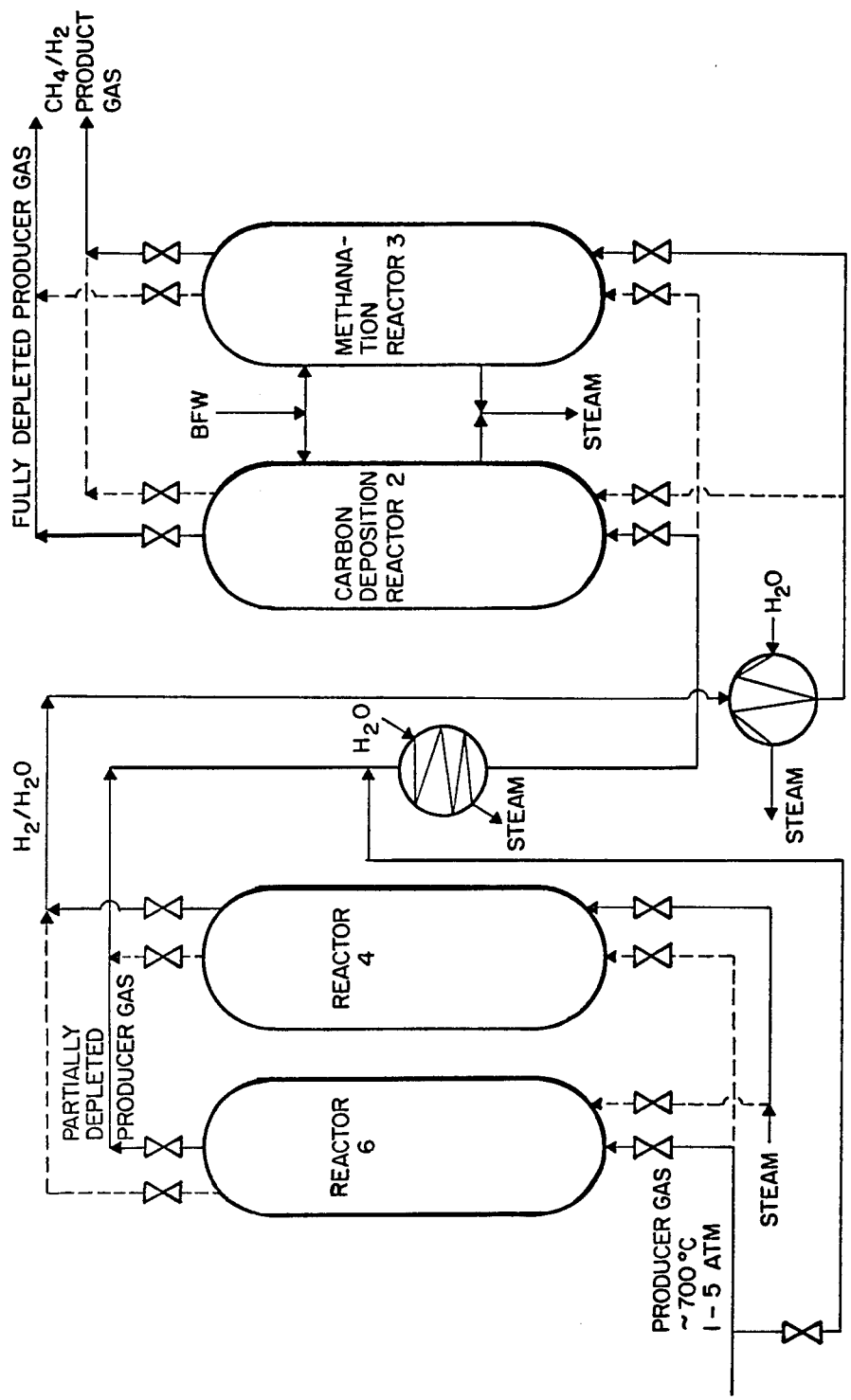
FIG. 6 schematically shows a third process for practicing the present invention

In FIG. 6, there is shown another alternative embodiment wherein the solids remain in the individual reactors, either as fixed beds or fluid beds, and the gas feed streams to the reactors are periodically switched between producer gas and steam-water. The reactors may be operated in one of the two modes, the first mode shown by the solid lines and the second mode shown by the broken lines. In the first mode, producer gas is fed into reduction reactor 6 where it contacts iron oxides. The partially depleted producer gas is then passed through a process steam boiler into reactor 2 where it contacts bulk iron to form the carbonaceous material. Simultaneously, steam is fed into hydrogen generator reactor 4 where it contacts reduced iron to form hydrogen gas. The hydrogen gas is then passed into methanation reactor 3 where it contacts previously formed carbonaceous material to form methane. At selected intervals, the gas feeds to reactors 2, 3, 4, and 6 are switched. As shown by the dotted line, hydrogen which is formed in reactor 6 passes into reactor 2 causing the formation of methane from the reaction of hydrogen with the carbonaceous material. The depleted producer gas passes from reactor 4 and into reactor 3 to form the carbonaceous material.

Figure 7:
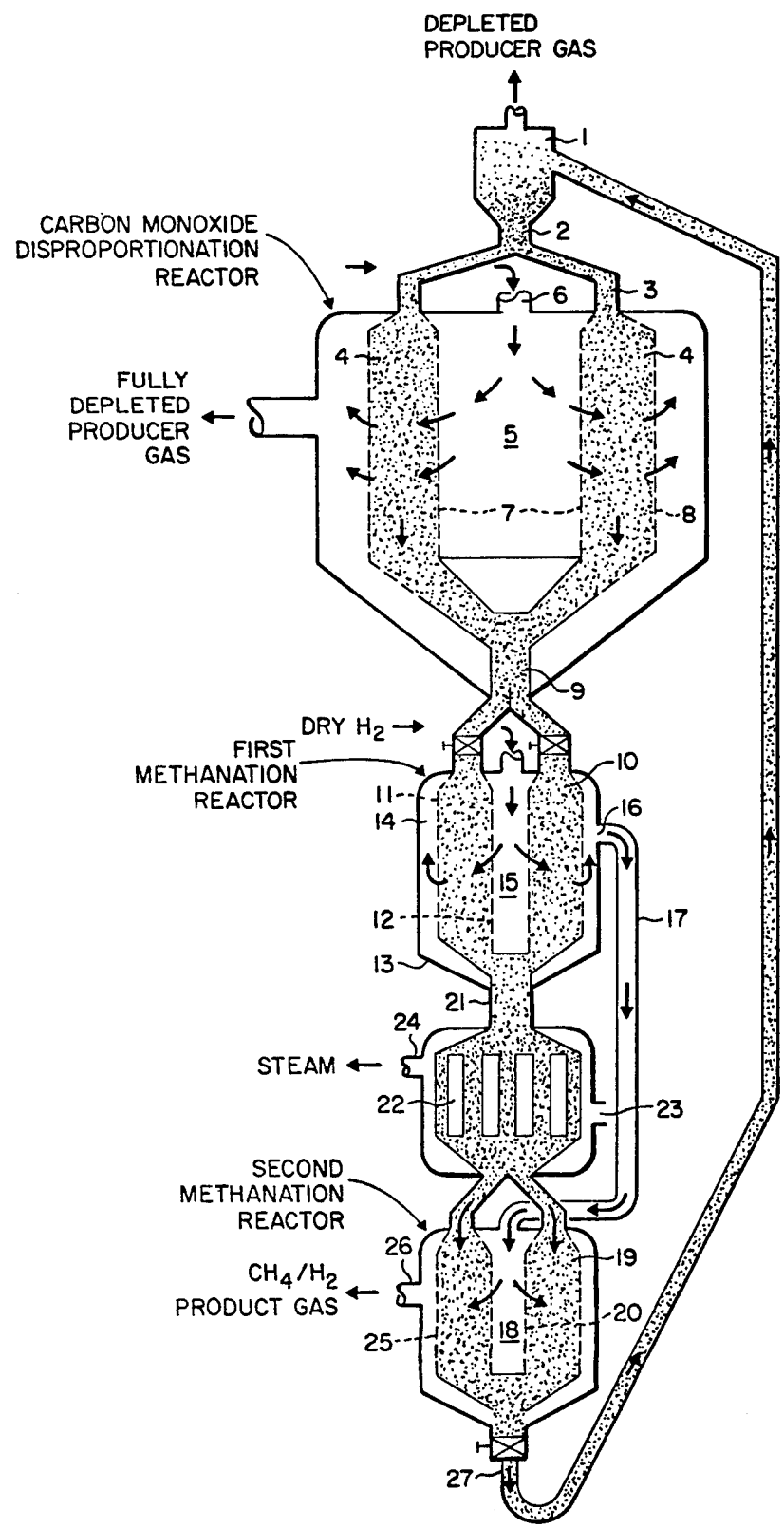
FIG. 7 schematically shows a fourth process for practicing the present invention.

In FIG. 7 there is shown another embodiment of our invention in which partially depleted producer gas is used to produce a methane-rich gas in a single reactor shown in cross section. In this apparatus porous walled reaction cyclinders are used, the pores of which allow passage of gas therethrough but are too small to permit passage of our solid carbonaceous material or the bulk iron carrying the carbonaceous material. The preferred form of bulk disproportionation initiators is iron spheres.

The iron spheres are initially located within a hopper 1 having an outlet 2 at the bottom through which the spheres are conveyed by gravity into passageway 3 and then into porous walled carbon deposition reactor 4 having a cavity 5 inside. At the top of cavity 5 is a gas inlet 6 for passage into cavity 5 of a partially depleted producer gas. The partially depleted producer gas passes through inside porous walls 7 into reactor 4 where the gas contacts the iron catalyst for a sufficient length of time, at a pressure and temperature to form our carbonaceous material on the spheres. Thereafter, the fully depleted producer gas passes through the openings or pores of outside porous wall 8.

At the bottom of reactor 4 is outlet 9 through which the spheres carrying the carbonaceous material pass into methanation reactor 10 which is defined by outside gas porous wall 11, and inside gas porous wall 12. Coaxially surrounding the outside porous wall 11 is impervious wall 13 which, with wall 11, defines an annular chamber 14. Hydrogen gas flows through gas inlet 16 and into cavity 15 where the hydrogen passes through the openings of inside porous wall 12 and into contact with the carbonaceous material in methanation reactor 10 to form a methane-rich gas. This methane-rich gas then passes out of reactor 10 through the openings in outside gas porous wall 11, into cavity 14, then through gas outlet 16, into gas transfer pipe 17 which transfers it to cavity 18 located within a second methanation reactor 19. The cavity 18 and reactor 19 are separated by inside gas porous wall 20.

The partially carbon depleted carbonaceous solid material from methanation reactor 10 passes out of reactor 10 via solids outlet 21 and is cooled with water in solids cooler 22 by passing water into cooler 22 through water inlet 23 to produce steam which passes out of the cooler through steam outlet 24. The cooled solids then pass into the second methanation reactor 19 where they are again contacted with the methane-hydrogen gas passing through porous wall 20 to further react with the carbonaceous material to form methane. The enriched methane-containing gas passes out of second methanation reactor 19 through outside porous wall 24 and gas outlet 26. Carbon depleted iron-carbonaceous solids are then transferred to solids hopper 1 via lift return 27 to be used again in the process.

Figure 16:
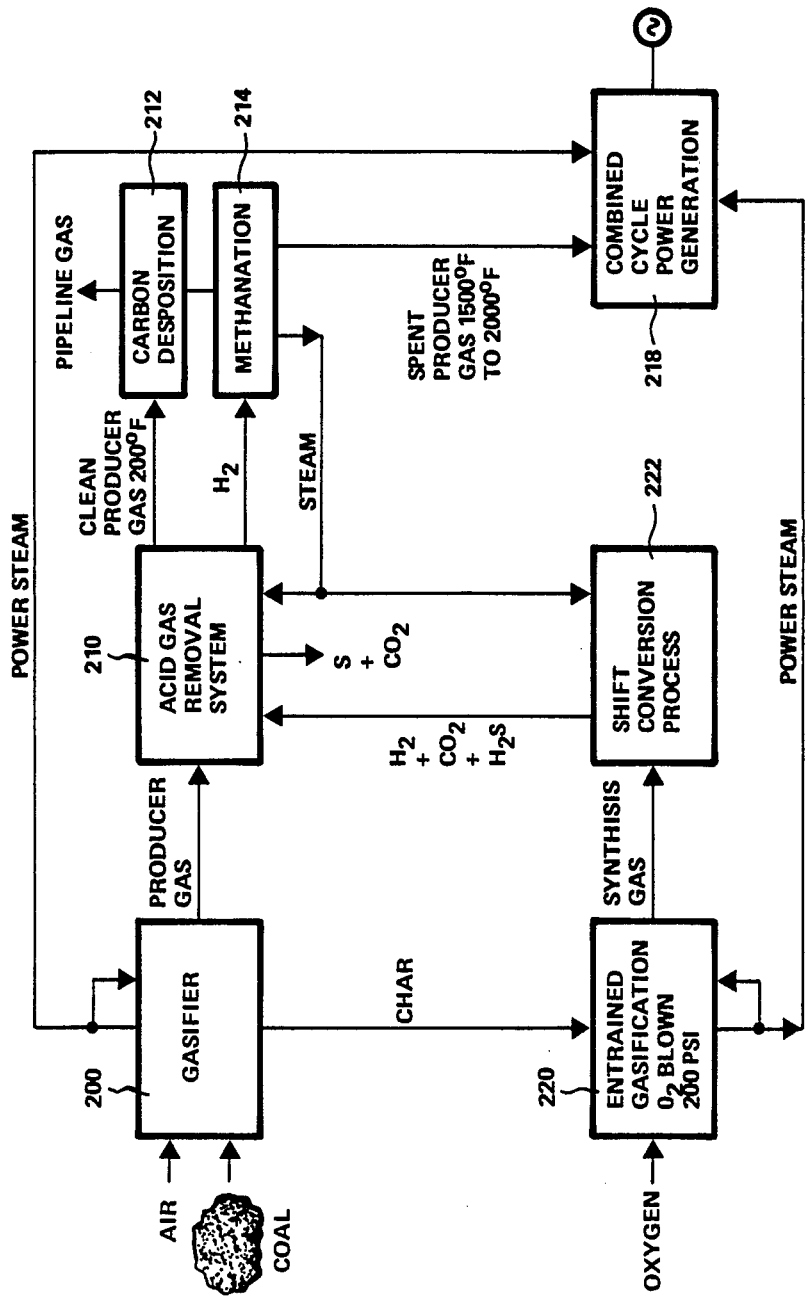
FIG. 16 schematically shows a sixth process for practicing the present invention.

FIG. 16 shows schematically another alternate embodiment of our process for making methane in which the hydrogen is derived by the shift conversion of steam and carbon monoxide. This is a conventional process in which carbon monoxide and steam react in the presence of catalysts such as cobalt and molybdenum to form hydrogen and carbon dioxide.

In this process, coal is burned in air in gasifier 200 to provide the producer gas which passes through an acid gas removal system 210 to remove carbon dioxide and sulfur from the producer gas. The clean producer gas is forwarded to the carbon deposition reactor 212 where it is disproportionated to provide carbon-rich solids which are fed to the methane reactor 214. The carbonaceous material is then reacted with hydrogen to produce methane. A portion of the excess heat generated in the reactors 212 and 214 is used to provide steam which is forwarded to the shift conversion reactor 222 and gas removal system 210. Spent producer gas is forwarded to a power generation system 218 to provide electricity.

When the coal is burned in the gasifier 200, in addition to forming the producer gas, a char is formed which is oxidized in a second gasifier 220 using essentially pure oxygen under conditions which favor the formation of a synthesis gas including carbon monoxide. The carbon monoxide is reacted with the steam in a shift conversion reactor 222 to provide the hydrogen. In addition to hydrogen, carbon dioxide and hydrogen sulfide are formed. These gases are forwarded to the acid gas removal system 210 for removal of sulfur and carbon dioxide. Heat energy from the gasification of the coal and char is also used to drive the power generation system 218.

The process depicted in FIG. 16 avoids handling large quantities of iron solids as required in the steam-iron process for producing hydrogen; however, it does not provide as much of heat at high temperatures and requires the use of oxygen in the hydrogen production process. Nevertheless, the process depicted in FIG. 16 is more efficient in converting the heating value of the fuels used as feeds to electric power and carbonaceous material or electric power and methane. This is illustrated in FIGS. 17 and 18 (prior art), considered in conjunction with Table VIII.

Figure 17:
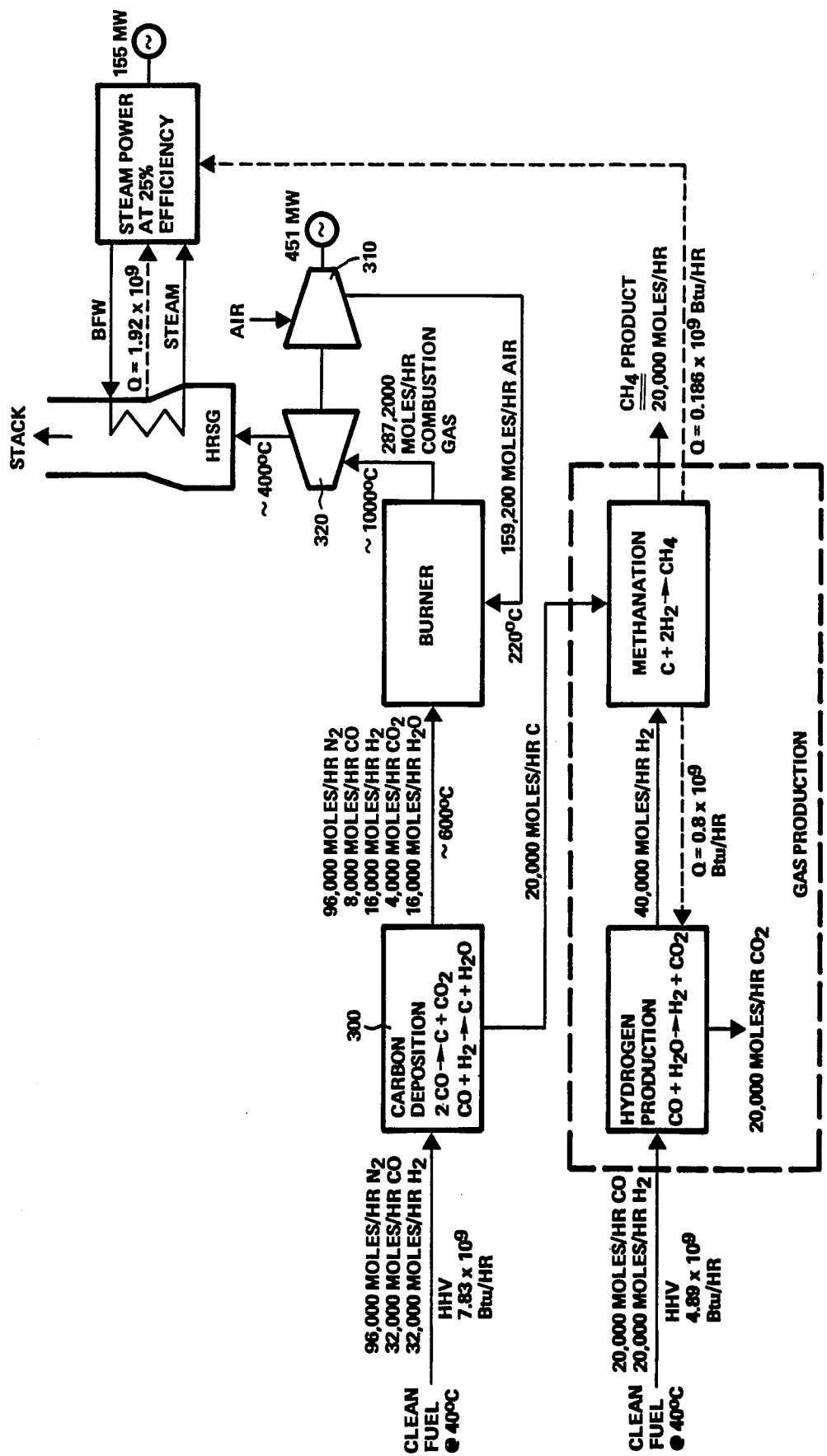
FIG. 17 shows another process for practicing the present invention.
Figure 18:
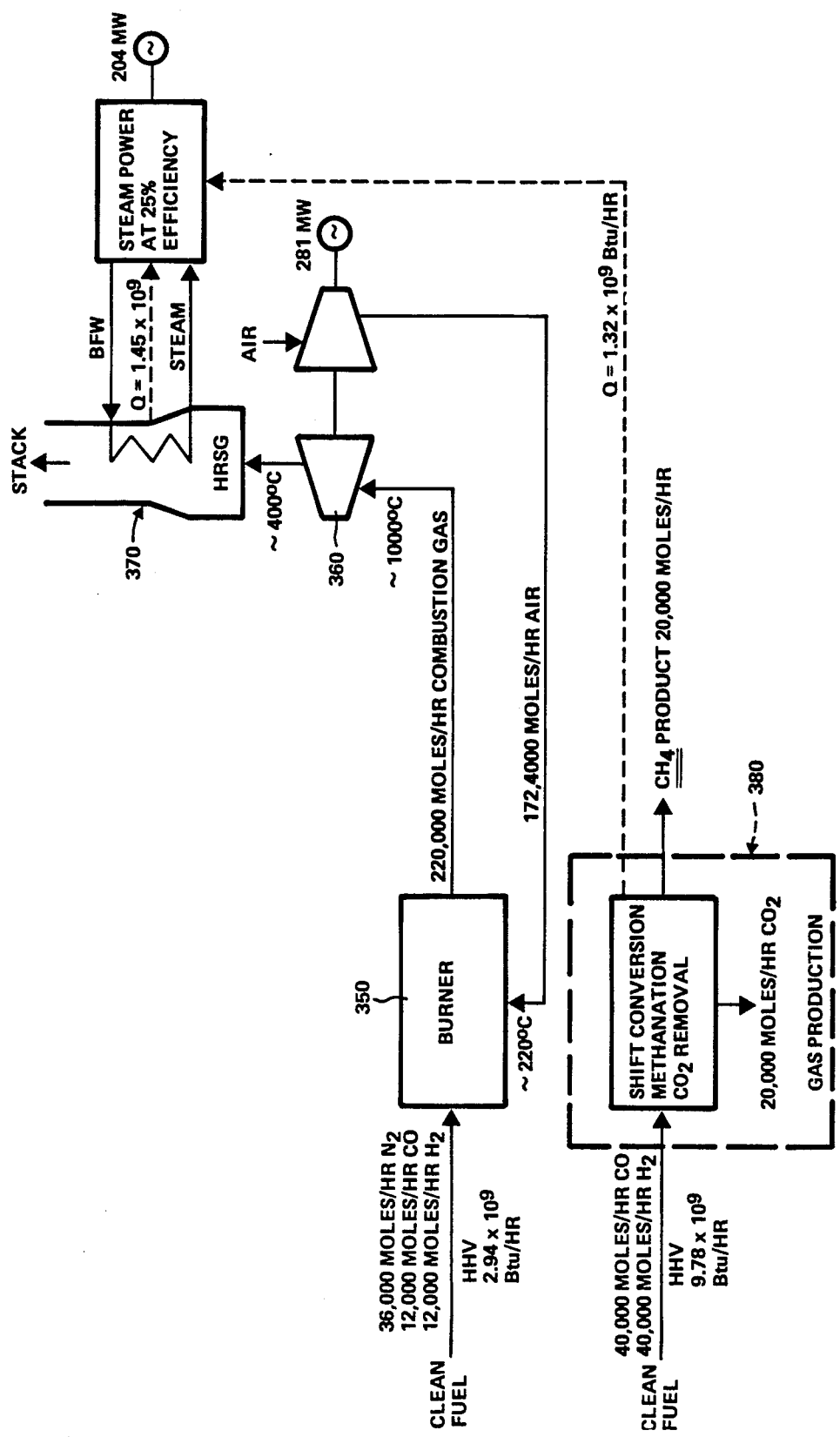
FIG. 18 shows a conventional system for obtaining high B.T.U. gas and combined cycle electric power.

The process depicted in FIGS. 16 and 17, as contrasted with the prior art process depicted in FIG. 18, is a synergistic combination of the coproduction of combined cycle electric power and a carbonaceous material which may be converted to methane. This synergism is illustrated by contrasting the heat and material balances and efficiency calculations of our process and the prior art. Both processes use the same total amount of fuel gas, total higher heating value (HHV), to produce 20,000 moles/hr of methane and as much coproduct electric power as possible.

As shown in FIG. 17, in our process a clean, low Btu fuel gas (100–300 Btu/standard cubic foot) consisting of 96,000 moles/hr $N_2$, 32,000 moles/hr CO, and 32,000 moles/hr $H_2$ is passed first to a fluid bed carbon deposition reactor 300 where disproportionation takes place and carbonaceous material is deposited and separated from the gas stream (20,000 moles/hr of carbon). This process step is at the heart of the synergism of our process. Since the fuel entering the carbon deposition reactor is also the working fluid for combined cycle power generation, we have achieved the following:

(i) Removed 20,000 moles per hour of carbon (and carbon heating value) from the combined cycle working fluid (higher heating value of the carbon $3.39 \times 10^9$ Btu/hr). This carbon, which has been removed from the combined cycle working fluid stream, is subsequently converted completely into methane product gas.

(ii) Effectively combusted to $CO_2$ and water vapor 4,000 moles of carbon monoxide and 16,000 moles of hydrogen. Essentially all of the heat of this combustion is retained within the combined cycle working fluid as sensible heat. Thus, we have removed the carbon (for our $CH_4$ product) from the combined cycle working fluid, but retained in the working fluid all of the heat of reaction associated with carbon deposition.

(iii) The combined cycle efficiency in converting to electricity the remaining heating value and sensible heat left in the producer gas after carbon deposition surprisingly increases over the combined cycle efficiency of fuel gas fed directly to the burner. The reason for this is that, at a fixed gas turbine inlet temperature, (limited by material constraints) less air must be compressed by compressor 310 per mole of gas through the turbine 320 for the partially depleted gas from the carbon deposition reactor 300 than is the case if the fuel gas is fed directly to the burner.

After passing through the carbon deposition reaction 300, the depleted fuel gas is burned with excess air and the resulting combustion gases at 1,075° C. are expanded through the gas turbine 320 at an inlet pressure of about 15 atm down to near atmospheric pressure. The expanded gases leave the turbine 320 at about 525° C. and the remaining sensible heat left in the combustion gases are used to generate steam in the heat recovery steam generator 330. Subsequent steam derived electric power is at an estimated heat-to-electricity efficiency of 25%.

As described, the 20,000 moles/hr of carbon removed from the combined cycle working fluid are directly hydrogenated to methane by hydrogen derived from an intermediate Btu gas (20,000 moles/hr of CO+20,000 moles/hr of $H_2$) by shift conversion and subsequent removal of carbon dioxide. Of the overall heat generated by methanation and shift conversion ($0.986 \times 10^9$ Btu/hr), $0.8 \times 10^9$ Btu/hr are required for generating steam for the shift conversion reaction and the remaining $0.186 \times 10^9$ Btu/hr are assumed to be convertible to steam derived electric power at 25% efficiency.

FIG. 18 shows a conventional system for obtaining high Btu gas and combined cycle electric power. In the conventional system 36,000 moles/hr nitrogen, 12,000 moles/hr nitrogen, 12,000 moles/hr CO (HHV $2.94 \times 10^9$ Btu/hr) are fed to a burner 350 and burned with excess air. The resulting combustion gases at 1,075° C. are expanded through gas turbines 360 and passed on to heat recovery systems 370 to generate combined cycle electric power. In the conventional system, a second portion of fuel gas, 40,000 moles/hr of CO plus 40,000 moles per hour of hydrogen, (HHV $9.78 \times 10^9$ Btu/hr) are fed to shift conversion reactors and $CO_2$ removal reactors 380 resulting in a shifted gas with a $H_2$:CO ratio of 3:1. This gas is next converted to methane in a conventional methanation reactor (also designated as 380). The total heat released in these reactors is $2.12 \times 10^9$ Btu/hr of which $0.8 \times 10^9$ Btu/hr is required for generating shift conversion steam and $1.32 \times 10^9$ Btu/hr is assumed to be available for steam derived electric power conversion at an efficiency of 25%.

Table VIII compares the efficiencies and power generated for our process and the conventional process. In both systems the same amount of total fuel heating value is fed ($12.73 \times 10^9$ Btu/hr) and methane product produced (20,000 moles/hr of $CH_4$). However, in our process 606 megawatts (MW) of electric power are produced versus 485 MW for the conventional system. This difference in power generation is the direct result of the difference in overall efficiency (40.8% vs. 32.6%) in converting all heating values (exclusive of methane product) to electric power. The synergism associated with the increased combined cycle efficiency of converting the remaining fuel value and sensible heat of the depleted fuel gas in our process to electric power is also shown. For our system, the combined cycle

TABLE VIII

|  | OUR PROCESS | PRIOR ART |
|---|---|---|
| TOTAL FUEL FED TO SYSTEMS | $12.72 \times 10^9$ Btu/HR | $12.72 \times 10^9$ Btu/HR |
| TOTAL CH$_4$ PRODUCED | 20,000 MOLES/HR | 20,000 MOLES/HR |
| MOLES FUEL GAS REQUIRED PER MOLE CH$_4$ PRODUCED | 3 | 4 |
| COLD GAS EFFICIENCY (CGE) IN GAS PRODUCTION (HHV CH$_4$/HHV FUEL IN) | 92.3%$^{(a)}$ | 78.2% |
| WASTE HEAT RELEASED IN GAS PRODUCTION (NET) | $.186 \times 10^9$ | $1.32 \times 10^9$ |
| TOTAL GAS TURBINE POWER | 451 MW | 281 MW |
| TOTAL STEAM TURBINE POWER | 155 MW | 204 MW |
| TOTAL POWER | 606 MW | 485 MW |
| COMBINED CYCLE EFFICIENCY (CCE) 90% (LHV) | 55.3 | 48.9$^{(b)}$ |
| TOTAL EFFICIENCY (TE) IN CONVERTING ALL HEATING VALUES EXCLUSIVE OF CH$_4$ PRODUCT TO ELECTRIC POWER | 40.8%$^{(c)}$ | 32.6% |

$$^{(a)}CGE = \frac{HHV\ 20{,}000\ MOLES\ CH_4}{HHV\ 20{,}000\ CO + HHV\ 20{,}000\ H_2 + HHV\ 20{,}000\ C}$$

$$= \frac{7.66 \times 10^9}{4.89 \times 10^9 + 3.39 \times 10^9} = 92.3\%$$

$$^{(b)}CCE = \frac{HEAT\ EQUIVALENT\ OF\ POWER\ OUT}{LHV\ FUEL\ IN}$$

$$= \frac{281{,}000\ KW\text{-}HR \times 3413\ Btu/KW\text{-}HR + .25 \times 1.45 \times 10^9\ Btu}{2.71 \times 10^9\ Btu} = 48.9\%$$

$$^{(c)}TE = \frac{HEAT\ EQUIVALENT\ OF\ POWER\ OUT}{HHV\ OF\ FUEL\ IN - HHV\ CH_4\ PRODUCT}$$

$$= \frac{606{,}000\ KW\text{-}HR \times 3413\ Btu/KW\text{-}HR}{12.72 \times 10^9\ Btu - 7.66 \times 10^9\ Btu} = 40.8\%$$

efficiency in converting the lower heating value and sensible heat of the depleted fuel gas fed to the burner to electric power is 55.3%. In the conventional system the efficiency of converting the lower heating value of the fuel fed to the burner to electricity is 48.9%.

On the gas production side of the processes, our system generates less than half as much heat as the conventional process. The process generated heat is expensive to handle and can only be converted to electric power at relatively low efficiency (~25%). This result is reflected in the fact that the cold gas efficiency (heating value of methane/heating value of fuel gas and carbon) around the gas production part of our combined process is 92.3% vs. 78.2% for the conventional process.

FIG. 17 is used only as a simplified illustration of the synergistic advantages of combining our high Btu gas process with the coproduction of combined cycle electric power. Simplified gas feeds and extents of reaction were used and the individual blocks in the Figure represent, in some cases, several unit operations (e.g., shift conversion and methanation). This will be apparent to those skilled in the art. However, the general principles demonstrated herein will also apply well to systems with more complex feed gases and product compositions.

We claim:

1. A fibrous carbonaceous material comprising partially graphitized carbon formed by disproportionation of carbon monoxide at a temperature above 400° C. to about 700° C. at a pressure of about 1 to about 100 atmospheres over a metallic initiator comprising initiator alloy, the initiator alloy comprising at least two of iron, cobalt, and nickel, the fibrous carbonaceous material comprising from about 30 to about 99.5% by weight carbon and from about 0.5 to about 70% by weight ferrous group metal component, the ferrous group metal component comprising a product alloy comprising at least two of iron, cobalt, and nickel, the fibrous carbonaceous material including a major phase and a minor phase, the minor phase being nodules which are dispersed throughout the major phase and are intimately associated with and at least partly bonded to the carbon in the major phase, the minor phase comprising the ferrous metal product alloy.

2. The material of claim 1 in which the initiator alloy comprises about 50 parts by weight iron and about 50 parts by weight of another ferrous group metal.

3. The material of claim 2 in which the initiator alloy comprises about 50 parts by weight iron and about 50 parts by weight nickel.

4. The material of claim 1 in which the initiator comprises iron/cobalt alloy.

5. The material of claim 1 in which the product alloy is an iron/nickel alloy.

6. The material of claim 5 in which the product alloy comprises about 50 parts by weight iron and about 50 parts by weight nickel.

7. The material of claim 1 in which the product alloy is an iron/cobalt alloy.

8. The material of claim 1 in which the product alloy is an iron/nickel/cobalt alloy.

9. The material of claim 1 in which the diameter of the fibers is up to about 2 microns.

10. The material of claim 9 in which the diameter of the fibers is from about 0.02 to about 2 microns.

11. The material of claim 10 in which the length to diameter ratio of the fibers is greater than about 5:1.

12. The material of claim 1 in which the length to diameter ratio of the fibers is greater than about 5:1.

13. The material of claim 1 comprising at least about 2% by weight of the ferrous group metal component.

14. The material of claim 13 comprising at least about 5% by weight ferrous group metal component.

15. The material of claim 1 in which the ferrous group metal component is an alloy comprising about 50 parts by weight of the iron and about 50 parts by weight of another ferrous group metal.

16. A fibrous carbonaceous material comprising partially graphitized carbon formed by disproportionation of carbon monoxide at a temperature above 400° C. to about 700° C. at a pressure of about 1 to 100 atmospheres over a metallic initiator comprising initiator alloy, the initiator alloy comprising at least two of iron, cobalt, and nickel, the fibrous carbonaceous material comprising from 30 to 95% by weight carbon, from 5 to 70% by weight ferrous group metal component comprising a product alloy comprising at least two of iron, cobalt, and nickel, the fibrous carbonaceous material including a major phase and a minor phase, the major phase comprising carbon, the minor phase being nodules which are dispersed throughout the major phase and are intimately associated with and at least partly bonded to the carbon in the major phase, the minor phase comprising the ferrous metal product alloy.

17. The material of claim 16 in which the initiator alloy comprises about 50 parts by weight iron and about 50 parts by weight of another ferrous group metal.

18. The material of claim 17 in which the initiator alloy comprises about 50 parts by weight iron and about 50 parts by weight nickel.

19. The material of claim 16 in which the initiator comprises iron/cobalt alloy.

20. The material of claim 16 in which the product alloy is an iron/nickel alloy.

21. The material of claim 20 in which the product alloy comprises about 50 parts by weight iron and about 50 parts by weight nickel.

22. The material of claim 16 in which the product alloy is an iron/cobalt alloy.

23. The material of claim 16 in which the product alloy is an iron/nickel/cobalt alloy.

24. The material of claim 16 in which the ferrous group metal component is an alloy comprising about 50 parts by weight iron and about 50 parts by weight of another ferrous group metal.

* * * * *